United States Patent
Kühne et al.

(10) Patent No.: US 10,344,053 B2
(45) Date of Patent: Jul. 9, 2019

(54) INHIBITORS FOR INHIBITING TUMOR METASTASIS

(71) Applicants: Forschungsverbund Berlin e.V., Berlin (DE); Universität zu Köln, Köln (DE)

(72) Inventors: Ronald Kühne, Berlin (DE); Hans-Günther Schmalz, Brühl (DE); Matthias Müller, Berlin (DE); Cedric Reuter, Köln (DE); Arne Soicke, Overath (DE); Robert Opitz, Berlin (DE); Matthias Barone, Berlin (DE); Hartmut Oschkinat, Berlin (DE)

(73) Assignees: FORSCHUNGSVERBUND BERLIN E.V., Berlin (DE); UNIVERSITÄT ZU KÖLN, Köln (DE)

( * ) Notice: Subject to any disclaimer, the term of this patent is extended or adjusted under 35 U.S.C. 154(b) by 0 days.

(21) Appl. No.: 15/535,002

(22) PCT Filed: Dec. 11, 2015

(86) PCT No.: PCT/EP2015/079410
§ 371 (c)(1),
(2) Date: Jun. 9, 2017

(87) PCT Pub. No.: WO2016/092069
PCT Pub. Date: Jun. 16, 2016

(65) Prior Publication Data
US 2017/0320910 A1 Nov. 9, 2017

(30) Foreign Application Priority Data
Dec. 11, 2014 (DE) .......................... 10 2014 118 413

(51) Int. Cl.
*A61K 31/55* (2006.01)
*C07D 471/10* (2006.01)
*C07K 7/06* (2006.01)
*C07D 519/00* (2006.01)
*A61K 38/00* (2006.01)

(52) U.S. Cl.
CPC .............. *C07K 7/06* (2013.01); *C07D 519/00* (2013.01); *A61K 38/00* (2013.01)

(58) Field of Classification Search
CPC ............................. A61K 31/55; C07D 471/10
USPC ...................................... 514/212.05; 540/521
See application file for complete search history.

(56) References Cited

FOREIGN PATENT DOCUMENTS

| WO | WO 98/54208 A1 | 12/1998 |
| WO | WO 2008/040332 A1 | 4/2008 |
| WO | WO 2013/030111 A1 | 3/2013 |

OTHER PUBLICATIONS

Opitz, et al. 2015 "A modular toolkit to inhibit proline-rich motif-mediated protein-protein interactions" *Proceedings of the National Academy of Sciences* 112(16): 5011-5016.

*Primary Examiner* — Brenda L Coleman
(74) *Attorney, Agent, or Firm* — Knobbe, Martens, Olson & Bear LLP

(57) ABSTRACT

The present invention relates to chemical compounds that can in particular be used as structural mimetics of proline-rich peptides. The compounds of the present invention are capable of selectively inhibiting ena/VASP-EVH1-mediated protein-protein interactions. The invention further relates to the use of said compounds as pharmaceutical agents and to the use of the pharmaceutical agents to treat tumor diseases. The chemical compounds of the present invention can significantly inhibit the chemotaxis and motility of invasive tumor cells and can therefore be used in the treatment and/or prevention of tumor metastases.

19 Claims, 7 Drawing Sheets

A

B

INHIBITORS FOR INHIBITING TUMOR METASTASIS

Figure 1:
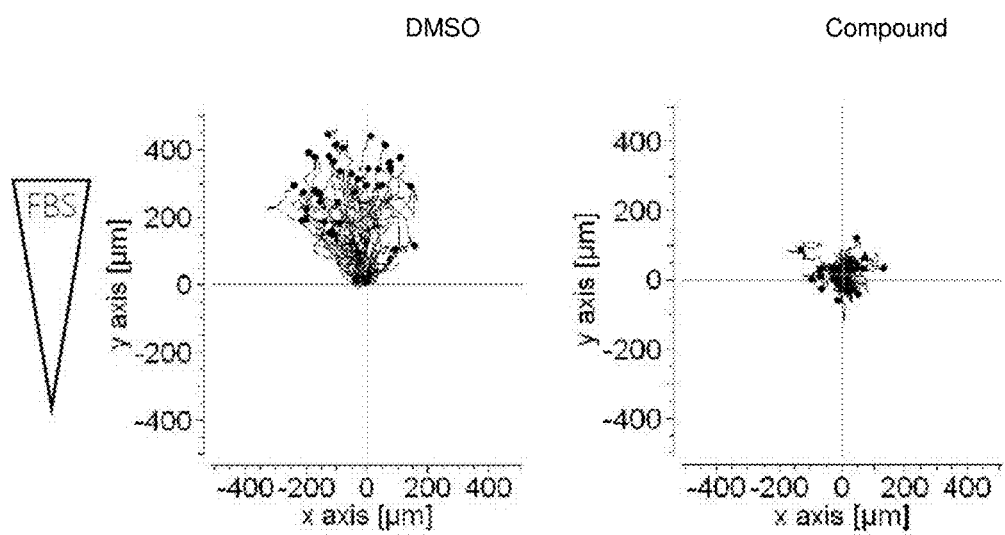
Figure 1:
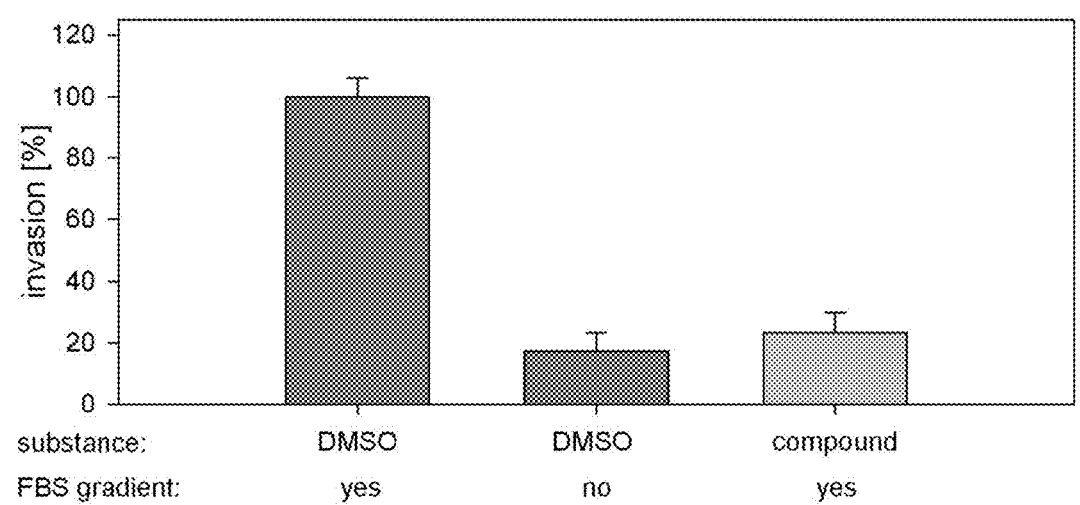

The present invention relates to chemical compounds that can in particular be used as structural mimetics of proline-rich peptides. The compounds of the present invention are capable of selectively inhibiting enaNASP-EVH1-mediated protein-protein interactions. The invention further relates to the use of said compounds as pharmaceutical agents and to the use of the pharmaceutical agents to treat tumor diseases. The chemical compounds of the present invention can significantly inhibit the chemotaxis and motility of invasive tumor cells and can therefore be used in the treatment and/or prevention of tumor metastases.

BACKGROUND TO THE INVENTION

Interactions between proteins play a pivotal role in almost all physiological and biochemical processes in living organisms. Proteins fulfill not only biocatalytic tasks (for example, as an enzyme), but rather are involved in a variety of biological processes. Selective inhibition of the physical interaction between peptide ligands and the corresponding protein receptors may have a significant influence on a variety of biological mechanisms in the cell.

In the state of the art there is therefore the need, in particular in the treatment of diseases, to develop molecules that inhibit specific protein-protein interactions in order to achieve biologically, i.e. medically, relevant technical effects.

Structural mimetics of diproline units are one example of such inhibitors. Based on its chemical structure, proline takes on a special role in comparison to other amino acids. Proline is the only secondary, proteinogenic amino acid that, after establishing a peptide bond, has no free NH proton for the formation of hydrogen bridge bonds. For this reason, polyproline sequences are unable to assume classic alpha helix or beta pleated sheet secondary structures. Due to these particular physical properties, polyproline amino acid sequences (e.g. proline-rich motifs (PRM)) are very well suited to initiate specific protein-protein interactions with receptors (e.g. proline-rich motifs binding domains (PBD)). By providing polyproline mimetics, a number of these interactions can be selectively inhibited.

A number of beta-turn peptidomimetics are known in the state of the art as modulators of protein-protein interactions. WO 2006/067091 A1 discloses a variety of peptides and peptidomimetics that prevent the homodimerization of MyD88 and the interaction between MyD88 and TIR. Beta-turn peptidomimetics are also known as modulators of protein-protein interactions between SH3 domains. WO 98/54208, for example, discloses that beta-turn peptidomimetics, which have polyproline motifs and an alpha-helix structure, can interact with SH3 domains. Witter et al (Bioorg. Med. Chem. Lett. 8 (1998) 3137) and Vartak et al (Organic Lett. 2006, 8:5, 983) disclose a variety of beta-turn peptidomimetics that can be used as mimetics for a polyproline sequence.

Other chemical compounds that function as diproline mimetics are disclosed in WO 2008/040332 and in WO 2013/030111. For example, WO 2013/030111 discloses peptide compounds that have two adjacent diproline mimetics instead of four proline amino acids, whereby the diproline mimetics are flanked by peptide sequences. The peptides described therein exhibit good affinity to a VASP-EVH1 domain but, due to their specific peptide structure, they are expensive to produce. Due to the peptide structure and the presence of endogenous proteases, the peptide structures continue to be decomposed in vivo. A number of these compounds also exhibit sub-optimal cell permeability, which is quite detrimental to use as a medicament.

Even though the compounds disclosed therein can inhibit protein-protein interactions by selective binding to a receptor, there is still a need to provide further polyproline mimetics that have improved binding properties and exhibit the corresponding biological effects.

DETAILED DESCRIPTION OF THE INVENTION

Therefore, in light of the state of the art, it was the task of the invention to provide compounds that can be used as mimetics for polyproline-rich peptides, in particular as pharmaceutical agents for the treatment of a variety of diseases. A further task of the invention was to provide novel anti-cancer drugs that act effectively against the invasion and motility of cancer cells.

The problem according to the invention is solved by providing a compound in accordance with Formula I:

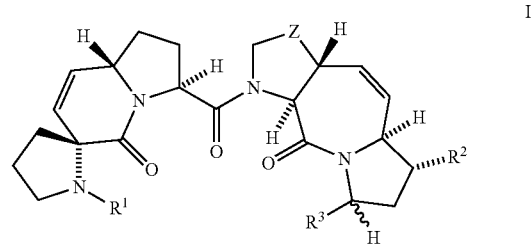

wherein
$R^1$: H, acyl, peptidyl, sulfonyl, alkyl, aryl, heteroaryl, wherein the acyl, peptidyl, sulfonyl, alkyl, aryl or heteroaryl substituents are optionally substituted in accordance with $R^1$;
$R^2$: H, alkyl, cycloalkyl, alkenyl, alkynyl, halogen, in particular F or Cl, O-alkyl, S-alkyl, aryl or heteroaryl, wherein the substituents are optionally substituted in accordance with $R^2$, for example fluoroalkyl or a heterocyclic substituent;
$R^3$: a C-containing substituent, for example alkyl, acyl, preferably a carboxylic acid derivative in accordance with C(=O)X, wherein X=OH, O-alkyl, O-aryl, NRR' (with R, R'=H or alkyl), NROR' (with R, R'=H or alkyl) or heteroaryl;
Z: $CH_2$ or $CH_2CH_2$, preferably $CH_2$.

Optional substitution refers to possible further residual groups, which may be present on the named residual groups of positions $R^1$, $R^2$, $R^3$ or $R^4$. Possible optional substitutions can preferably be halogen, acyl, carboxyl, amino, carbamoyl, OH, O-alkyl, SH, S-alkyl, alkyl, aryl or heteroaryl. If $R^1$ were alkyl, for example, one substituted alkyl could be a fluoroalkyl. Preferred heteroaryl substituents are imidazole, triazole, tetrazole or oxazole.

It was surprising that the inventive compounds—in some embodiments, without flanking peptide structures—exhibit good affinity to the target, high cell permeability and high stability. In light of the state of the art, it was not expected that the absence of a flanking peptide structure at the $R^3$ position would not have negative effects on the affinity of the molecule to the target. The improvements of the affinity by the absence of the flanking peptide structures at the $R^3$ position were surprising. The inventive compounds also show surprisingly good activity against the motility and invasion of cancer cells, and thus constitute effective anti-cancer reagents that are suitable for clinical use.

The stereochemical configuration at the radical $R^3$ is preferably to be defined as follows (Formula I-a):

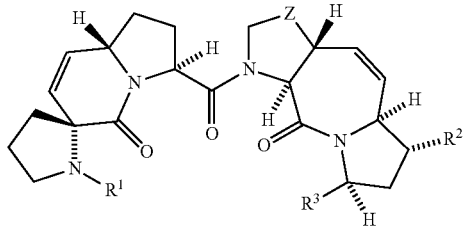

The substituents for $R^1$, $R^2$, $R^3$, Z are to be defined for Formula I-a as for Formula I (top).

A preferred embodiment of the present invention relates to compounds in accordance with the general Formula I or I-a, characterized in that $R^2$: alkyl, cycloalkyl, alkenyl, alkynyl, halogen, in particular F or Cl, O-alkyl, S-alkyl, aryl or heteroaryl, wherein the substituents are optionally substituted in accordance with $R^2$, for example fluoroalkyl or a heterocyclic substituent.

It was surprising that the inventive compounds do not exhibit the disadvantages of the state of the art. The inventive compounds have improved properties compared to the already known compounds; for example an improved ability to enter cells and thus an increased bioavailability. The metabolic stability of the inventive compounds is increased, and the strength of the bond to the target molecule and the high selectivity for the target molecule represent additional advantages of the inventive compounds.

A preferred embodiment of the present invention relates to a compound in accordance with the general Formula II:

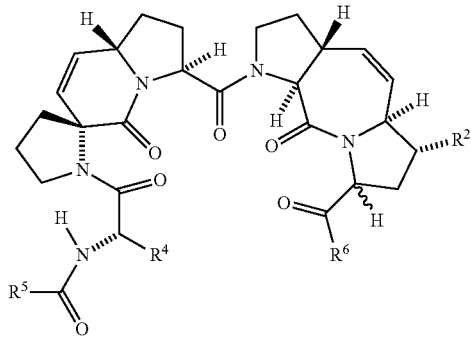

wherein
$R^2$: H, alkyl, cycloalkyl, alkenyl, alkynyl, halogen, in particular F or Cl, O-alkyl, S-alkyl, aryl or heteroaryl, wherein the substituents are optionally substituted in accordance with $R^2$, for example fluoroalkyl or a heterocyclic substituent;
$R^4$: H, alkyl, cycloalkyl, aryl or a heterocyclic substituent, preferably —$CH_2$-aryl or —$CH_2$-heteroaryl, for example —$CH_2$-phenyl, —$CH_2$-1-naphthyl or —$CH_2$-3-indolyl, wherein the substituents are optionally substituted in accordance with $R^4$;
$R^5$: H, alkyl or a substituted alkyl radical;
$R^6$: OH, O-alkyl, O-aryl, NRR' (with R, R'=H, alkyl), NROR' (with R, R'=H, alkyl) or heteroaryl.

The stereochemical configuration at the radical $COR^6$ is preferably to be defined as follows (Formula II-a).

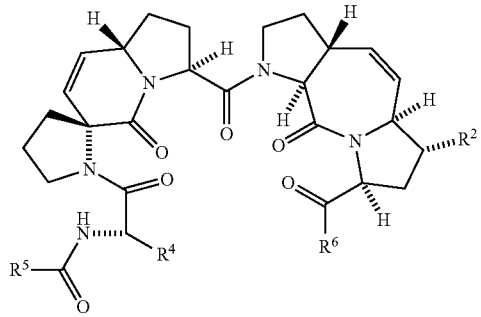

The substituents $R^2$, $R^4$, $R^5$, $R^6$ are to be defined for Formula II-a as for Formula II (top).

A preferred embodiment of the present invention relates to compounds in accordance with the general Formula II or II-a, characterized in that $R^2$: alkyl, cycloalkyl, alkenyl, alkynyl, halogen, in particular F or Cl, O-alkyl, S-alkyl, aryl or heteroaryl, wherein the substituents are optionally substituted in accordance with $R^2$, for example fluoroalkyl or a heterocyclic substituent.

In a preferred embodiment, the inventive compound in accordance with Formula I, I-a, II or II-a is characterized in that $R^2$: is alkyl, selected from the group $CH_3$, $C_2H_5$ or $C_3H_7$, preferably $CH_3$ or $C_2H_5$. These substituents make a particularly strong affinity to the target possible. Through the use of methyl or ethyl at the $R^2$ position, the molecule can dock perfectly in the binding pocket of the target, thereby imparting a much higher affinity.

It is further preferred that the substituent at the $R^2$ position has the stereochemistry shown in the graphic representation of the formula. This stereochemistry results in a particularly high affinity.

In a preferred embodiment, the inventive compound in accordance with Formula I, I-a, II or II-a is characterized in that $R^4$: is $CH_2$-aryl, in particular substituted —$CH_2$-phenyl, wherein the substituent is positioned at the ortho position of the phenyl group, wherein the substituent is preferably halogen, in particular Cl.

The substituent positioned at the $R^4$ position is preferably one that forms a 2-Cl-phenylalanine structure in the molecule (at the $R^1$ position of Formula I or I-a). Different halogens or ring structures can be used. Cl, F and Br are preferably used as the halogen. Methyl or other preferably short chain alkyl groups (e.g. $C_1$—$C_5$) can likewise be used as the substituent at the ortho position of the phenyl group.

In a preferred embodiment, the inventive compound in accordance with Formula II or II-a is characterized in that $R^6$: is O-alkyl, O-aryl, NRR' (with R, R'=H or alkyl), NROR' (with R, R'=H or alkyl) or heteroaryl. These substituents exhibit the advantage that they impart a much higher cell permeability, so that larger amounts of the active agent can be incorporated into the cell.

Under certain circumstances, the ester groups at the $R^6$ position can also be cleaved in vivo after administration by endogenous enzymes, so that there is a carboxyl group at the R6 position. The presence of the free carboxyl group at the $R^6$ position ($R^6$: OH) makes good affinity towards the target protein possible, but acts against the cell permeability of the molecule. "Pro-drugs", which exhibit good cell permeability and affinity for the target, can be created through esterification at this position. After cleavage of the molecule in vivo, these prodrugs can then produce a better bond, and thus a better effect.

The ethyl esters (R⁶: O-Et) are cleaved relatively quickly in vivo, while the methyl esters (R⁶: O-Me) and the amide (R⁶: NH₂) exhibit particularly good in vivo stability.

The presence of the NH₂ group at the R6 position also exhibits unexpectedly good cell permeability and affinity for the target.

In a preferred embodiment, the inventive compound in accordance with Formula II or IIa is characterized in that R⁶: is O—CH3, O—C2H5 or NH2. These substituents at the R⁴ position in particular, make an optimal combination of cell permeability and affinity possible that was not to be expected in light of the state of the art.

In further embodiments of the invention, the inventive compound is characterized by the Formulas III, IV, V, VI, VII or VIII:

III
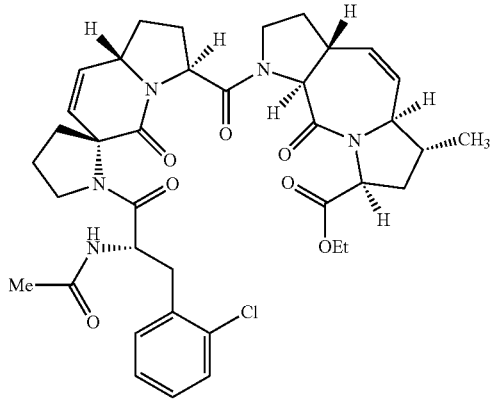

IV
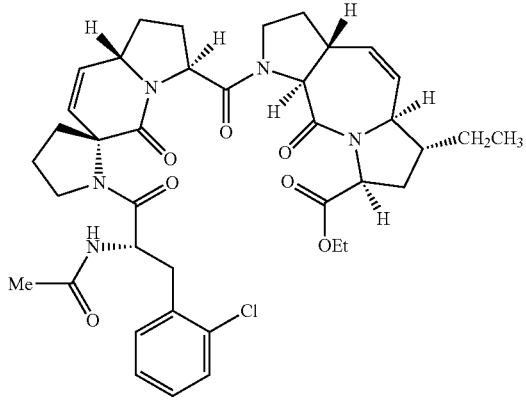

V
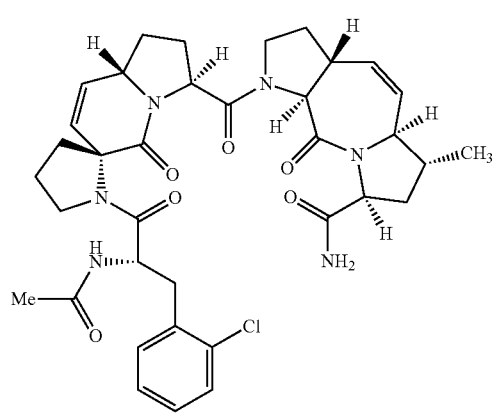

VI
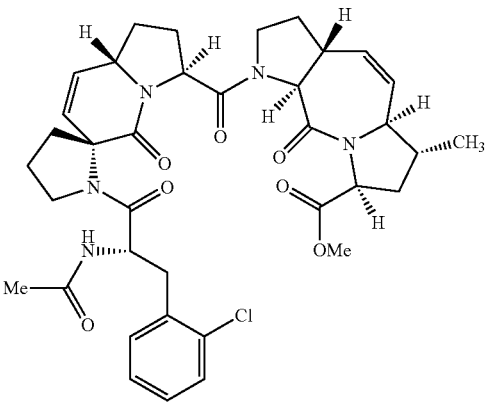

VII
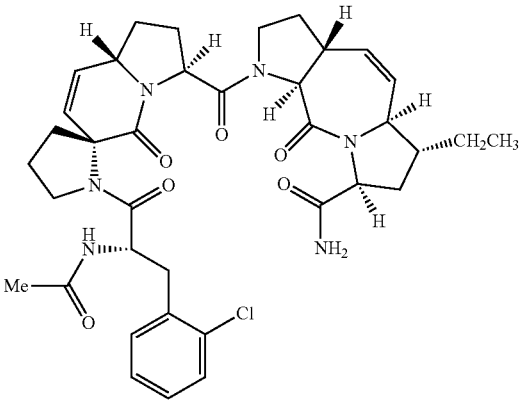

VIII
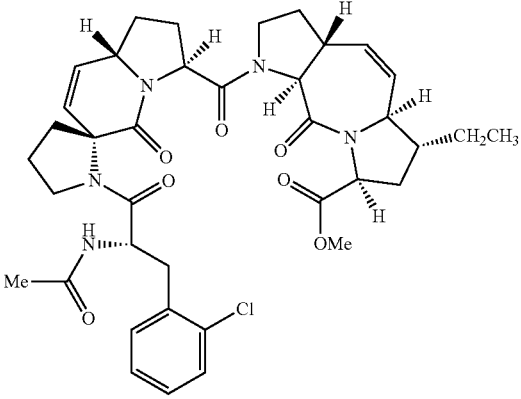

The invention relates to a compound as a ligand for an Ena/VASP-EVH1 domain. The EVH1 domain consists of about 115 amino acids and occurs in a large number of signaling multi-domain proteins. In addition to several others, this also includes the family of Ena/VASP proteins that act as molecular adapters and modulate the actin dynamics of the cytoskeleton. The EVH1 domains are divided into three classes according to their ligand preference. The first class recognizes in particular specifically a [F/W/L]PPPP core motif, which can be found in focal adhesion proteins such as vinculin, zyxin or RIAM, in lamellipodin, an important protein of the leading edge, in a number of proteins of the WAVE complex, as well as in the actA protein of the intracellular bacterium *Listeria monocytogenes*. Ena/VASP proteins are also found in filopodia and invadopodia, where they interact with their EVH1 domain with formins.

In another aspect, the invention relates to the use of the inventive compounds as a ligand for a domain selected from the group consisting of Src homology 3 domains, WW domains, GYF domains, UEV domains and/or profilin.

In one embodiment of the present invention, the compound is characterized in that the compound inhibits an Ena/VASP-EVH1-mediated protein-protein interaction. Accordingly, the invention also relates to the use of the novel structural mimetics of the polyproline-II helix as surprisingly good inhibitors of protein-protein interactions, in which in particular EVH1 domains, SH3 domains, WW domains, GYF domains UEV domains and profilin are involved. Proteins that contain these domains, such as VASP (EVH1 domain) or YAP (WW) play an important part in, among other things, the regulation of cell motility (in particular VASP) and cell proliferation (particularly YAP). VASP, for example, is strongly overexpressed in highly invasive breast cancer cells.

In one embodiment, the compound of the present invention is characterized in that the compound has a dissociation constant (Kd) in a complex with an Ena/VASP-EVH1 domain of ≤20 µM, preferably ≤2 µM, additionally preferred ≤500 nM. The particularly low dissociation constants constitute a surprising result. It was previously neither known nor mentioned in the state of the art that polyproline mimetics can exhibit such binding properties to EVH1 domains.

In a further aspect, the invention relates to a pharmaceutical composition comprising one or more inventive compounds, preferably with a pharmaceutically acceptable carrier. Preferred pharmaceutical carriers include, for example, fillers, extenders, binders, humectants, dissolution retarders, disintegrants, absorption accelerators, wetting agents, absorbents, and/or lubricants.

In a preferred aspect, the invention relates to the use of said compounds as pharmaceutical agents. Use as a pharmaceutical agent relates to use for surgical, therapeutic or diagnostic procedures. In a further aspect, the invention relates to a pharmaceutical means, which comprises the inventive compounds and, if need be, a pharmaceutically compatible carrier.

In a preferred embodiment of the invention, the compounds are used as polyproline mimetics. Advantageously, proline-rich amino acid sequences can in particular be found in peptides that are involved in signal transduction processes, in particular intracellular signal transduction processes. In the sense of the invention, the term mimetics can also be understood as analogs. The use of the inventive compounds is preferred for the treatment of diseases, which are associated with a modification of intracellular signal transduction processes that are mediated by polyproline helix structures, and are selected from the group comprising tumor diseases, bacterial infectious diseases and/or neurodegenerative diseases.

In another aspect, the invention relates to the use of the inventive compounds as a medicament for the treatment of tumor diseases. In a preferred embodiment of the invention, the tumor disease is breast cancer.

The use of an inventive compound as a medicament for the treatment of a tumor disease, is preferentially characterized in that the compound preferably inhibits the metastasis of a tumor by inhibition of the chemotaxis and/or motility of the tumor cells on the basis of a disruption of the actin filament synthesis.

It was completely surprising that the inventive compounds would exhibit a particularly good efficacy against the chemotaxis and/or motility of tumor cells. The inhibition of the chemotaxis and/or motility of tumor cells consequently plays a role, in particular, in the treatment and/or prevention of tumor metastases. This constitutes a technical effect that is different in comparison to that of the inhibition of cell proliferation.

Actin is a structural protein that occurs in all eukaryotic cells. It is a component of the cytoskeleton and one of the five most common proteins in eukaryotes. Actin forms dynamic actin filaments that are aligned as F-actin. These microfilaments aid in the stabilization of the external cell shape, the formation of cellular protuberances, intracellular relocations and directed cell movements. Many eukaryotic cells possess a high degree of mobility, referred to as cell motility or also cell migration, in order to, for example, be able to render intruders in the body harmless (cells of the immune system), heal wounds (e.g. skin cells) or to generally move cells (in development or in unicellular organisms such as amoebas). Cell migration also plays an essential role in cancer metastases. This mobility is based primarily on two processes: The directed actin polymerization in the direction of movement (controlled by a number of regulators that react to signals from the cell periphery), and the actin-myosin interaction in fibril bundles (stress fibers), contractile pull cords that pass through the cell and brace shaping elements to the substrate.

The disruption of actin filament synthesis caused by the inventive compounds likewise represents a new and advantageous technical effect. By disrupting actin filament synthesis, the inventive compounds can inhibit the motility of the cancer cells and thus strongly inhibit or prevent cancer metastasis.

The preferred tumor diseases are selected from the group encompassing tumors of the ear-nose-throat region, the lungs, the mediastinum, the gastrointestinal tract, the urogenital system, the gynecological system, the breast, the endocrine system, the skin, bone and soft tissue sarcomas, mesotheliomas, melanomas, neoplasms of the central nervous system, cancerous diseases or tumor diseases in childhood, lymphomas, leukemias, paraneoplastic syndromes, metastases with unknown primary tumor (CUP syndrome), peritoneal carcinomatoses, immunosuppression-related malignancies and/or tumor metastases.

The tumors may in particular be the following types of cancer: adenocarcinoma of the breast, the prostate and the colon; all forms of lung cancer starting in the bronchial tube; bone marrow cancer; melanoma; hepatoma; neuroblastoma; papilloma; apudoma; choristoma; branchioma; malignant carcinoid syndrome; carcinoid heart disease; carcinoma (for example, Walker carcinoma, basal cell carcinoma, basosquamous carcinoma, Brown-Pearce carcinoma, ductal carcinoma, Ehrlich tumor, carcinoma in situ, cancer-2 carcinoma, Merkel cell carcinoma, mucous cancer, non-small cell lung cancer, oat cell cancer, papillary carcinoma, scirrhous carcinoma, bronchioloalveolar carcinoma, bronchial carcinoma, squamous cell carcinoma and transitional cell carcinoma); histiocytic functional disorder; leukemia (e.g. in connection with B-cell leukemia, mixed-cell leukemia, null-cell leukemia, T-cell leukemia, chronic T-cell leukemia, HTLV-II-associated leukemia, acute lymphocytic leukemia, chronic lymphocytic leukemia, mast cell leukemia, and myeloid leukemia); malignant histiocytosis, Hodgkin's disease, non-Hodgkin lymphoma, solitary plasmacytoma; reticuloendotheliosis, chondroblastoma; chondroma, chondrosarcoma; fibroma; fibrosarcoma; giant-cell tumors; histiocytoma; lipoma; liposarcoma; leukosarcoma; mesothelioma; myxoma; myxosarcoma; osteoma; osteosarcoma; Ewing sarcoma; synovioma; adenofribroma; adenolymphoma; carcinosarcoma; chordoma; craniopharyngioma;

dysgerminoma; hamartoma; mesenchymoma; mesonephroma; myosarcoma; ameloblastoma; cementoma; odontoma; teratoma; thymoma; chorioblastoma; adenocarcinoma; adenoma; cholangioma; cholesteatoma; cylindroma; cystadenocarcinoma; cystadenoma; granulosa cell tumor; gynadroblastoma; hidradenoma; islet cell tumor; Leydig cell tumor; papilloma; Sertoli cell tumor; theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; non-chromaffin paraganglioma; angiokeratoma; angiolymphoid hyperplasia with eosinophilia; sclerosing angioma; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phyllodes; hemangiosarcoma; lymphangiosarcoma; myxosarcoma; ovarian cancer; sarcoma (for example Ewing sarcoma, experimental, Kaposi sarcoma and mast cell sarcoma); neoplasms (for example bone neoplasms, breast neoplasms, neoplasms of the digestive system, colorectal neoplasms, liver neoplasms, pancreas neoplasms, pituitary neoplasms, testicular neoplasms, orbital neoplasms, neoplasms of the head and neck, of the central nervous system, neoplasms of the acoustic organ, the pelvis, the respiratory tract and the urogenital tract); neurofibromatosis and cervical squamous epithelial dysplasia.

In a further preferred embodiment, the cancer or the tumor is selected from the group: tumors of the ear-nose-throat region, encompassing tumors of the inner nose, the nasal sinuses, the nasopharynx, the lips, the oral cavity, the oropharynx, the larynx, the hypopharynx, the ear, the salivary glands and paragangliomas, tumors of the lungs encompassing non-small cell lung cancer, small cell lung cancer, tumors of the mediastinum, tumors of the gastrointestinal tract encompassing tumors of the esophagus, the stomach, the pancreas, the liver, the gallbladder and the bile ducts, the small intestine, colon and rectal carcinomas and anal carcinomas, urogenital tumors encompassing tumors of the kidneys, the ureter, the bladder, the prostate, the urethra, the penis and the testicles, gynecological tumors encompassing tumors of the cervix, the vagina, the vulva, endometrial cancer, malignant trophoblastic disease, ovarian cancer, tumors of the fallopian tube, tumors of the abdominal cavity, mammary carcinomas, tumors of the endocrine organs encompassing tumors of the thyroid, the parathyroid, the adrenal cortex, endocrine pancreatic tumors, carcinoid tumors and carcinoid syndrome, multiple endocrine neoplasias, bone and soft tissue sarcomas, mesotheliomas, skin tumors, melanomas encompassing cutaneous and intraocular melanomas, tumors of the central nervous system, tumors during childhood, encompassing retinoblastoma, Wilms tumor, neurofibromatosis, neuroblastoma, Ewing sarcoma tumor family, rhabdomyosarcoma, lymphomas including non-Hodgkin lymphoma, cutaneous T-cell lymphomas, primary lymphomas of the central nervous system, Hodgkin's disease, leukemias encompassing acute leukemias, chronic myeloid and lymphatic leukemias, plasma cell neoplasms, myelodysplastic syndromes, paraneoplastic syndromes, metastases with unknown primary tumor (CUP syndrome), peritoneal carcinomatoses, immunosuppression-related malignancy including AIDS-related malignancies such as Kaposi sarcoma, AIDS-associated lymphomas, AIDS-associated lymphomas of the central nervous system, AIDS-associated Hodgkin's disease and AIDS-associated anogenital tumors, transplantation-related malignancies, metastasized tumors encompassing brain metastases, lung metastases, liver metastases, bone metastases, pleural and pericardial metastases, and malignant ascites.

In a further preferred embodiment, the cancer or tumor is selected from the group encompassing the cancers or tumor diseases mammary carcinomas, gastrointestinal tumors, including colon carcinomas, stomach cancer, pancreatic cancer, colon cancer, small intestinal cancer, ovarian cancer, cervical cancer, lung cancer, prostate cancer, renal cell carcinomas and/or liver metastases.

In the treatment of the named diseases, it is particularly preferred to prepare and/or use the pharmaceutical means, which comprises the inventive compounds, in the form of a gel, powder, tablet, modified-release tablet, premix, emulsion, infusion formulation, drops, concentrate, granulate, syrup, pellet, bolus, capsule, aerosol, spray and/or inhalant.

The pharmaceutical means, which comprises the inventive compounds, is preferably available in a preparation in a concentration of 0.1 to 99.5, preferably 0.5 to 95.0, particularly preferably 20.0 to 80.0 wt %.

The preparation is preferably administered orally, subcutaneously, intravenously, intramuscularly, intraperitoneally and/or topically.

The pharmaceutical means that contains the inventive compounds is preferably used in total quantities of 0.05 to 500 mg per kg, preferably 5 to 100 mg per kg body weight, every 24 hours.

The administration of the inventive compound or pharmaceutical composition to the patient is preferably oral, by injection, topically, vaginally, rectally and/or nasally.

The invention also relates to a kit, which comprises at least one of the inventive compounds and/or one of the inventive pharmaceutical means, if necessary with information for combining the contents of the kit—e. g. a package insert or an internet address that refers to home pages with further information etc. The information regarding the use of the kit may, for example, include a therapy outline for the above mentioned diseases, in particular for the preferred diseases. The information can, however, also include details about how the inventive products are to be used within a diagnosis of the named diseases. The inventive kit can also be used in basic research.

The invention also relates to the use of the kit for prophylaxis and/or therapy of neurodegenerative diseases, bacterial infectious diseases or tumor diseases.

FIGURES

FIG. 1: Inhibition of the chemotaxis and motility of highly invasive tumor cells in a matrigel migration assay.

Figure 2:
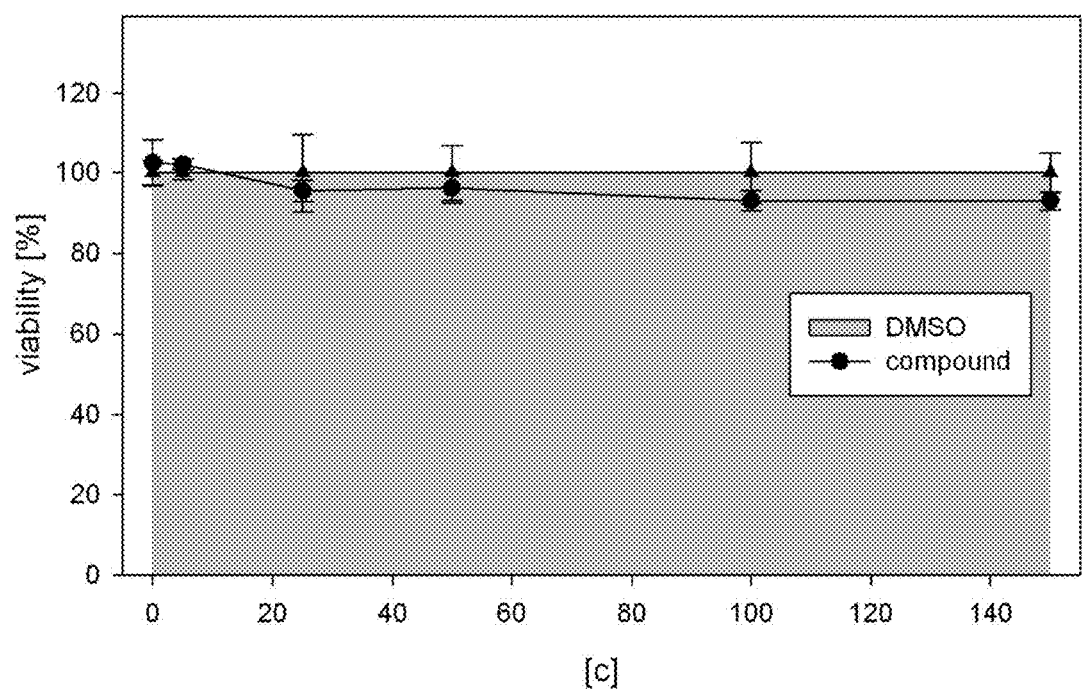

FIG. 2: Cellular toxicity of the compound in accordance with Formula III.

Figure 3:
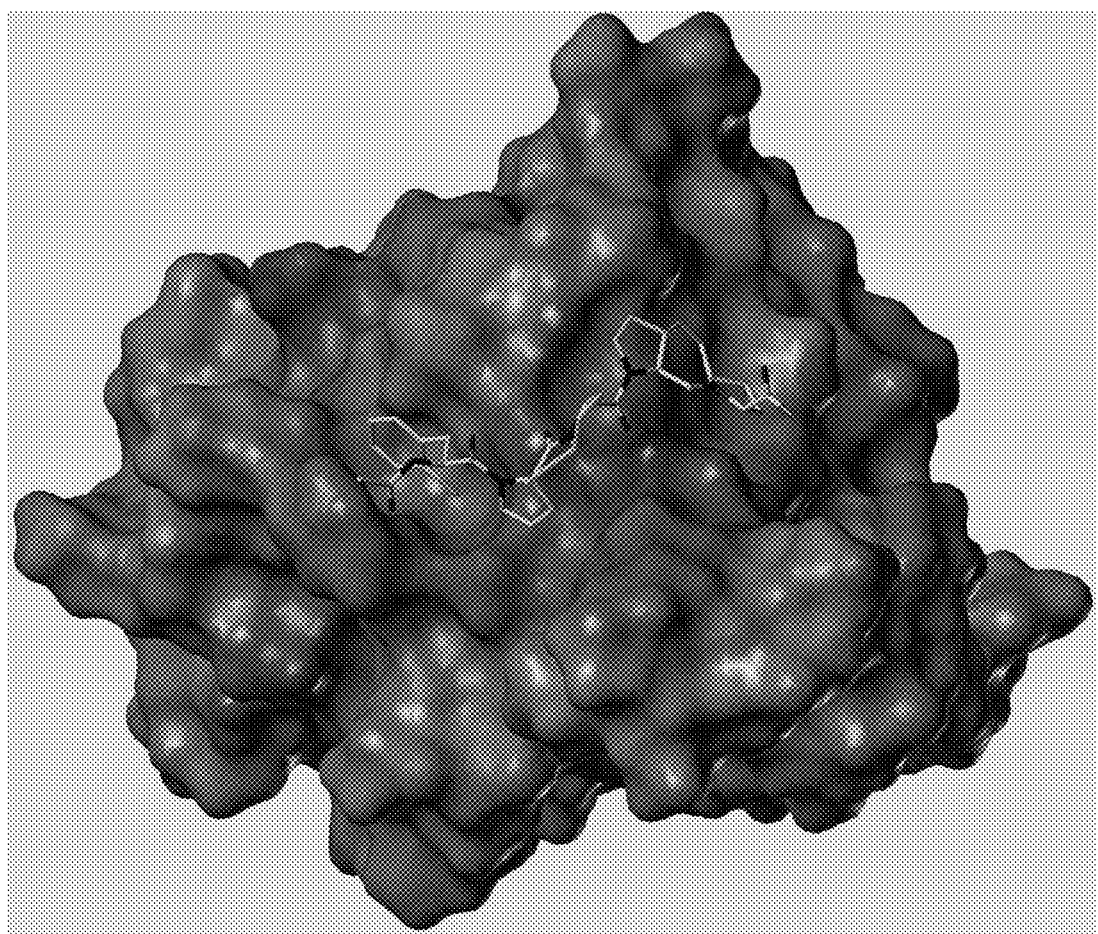

FIG. 3: Binding of the compound in accordance with Formula III to ena-EVH1.

Figure 4:
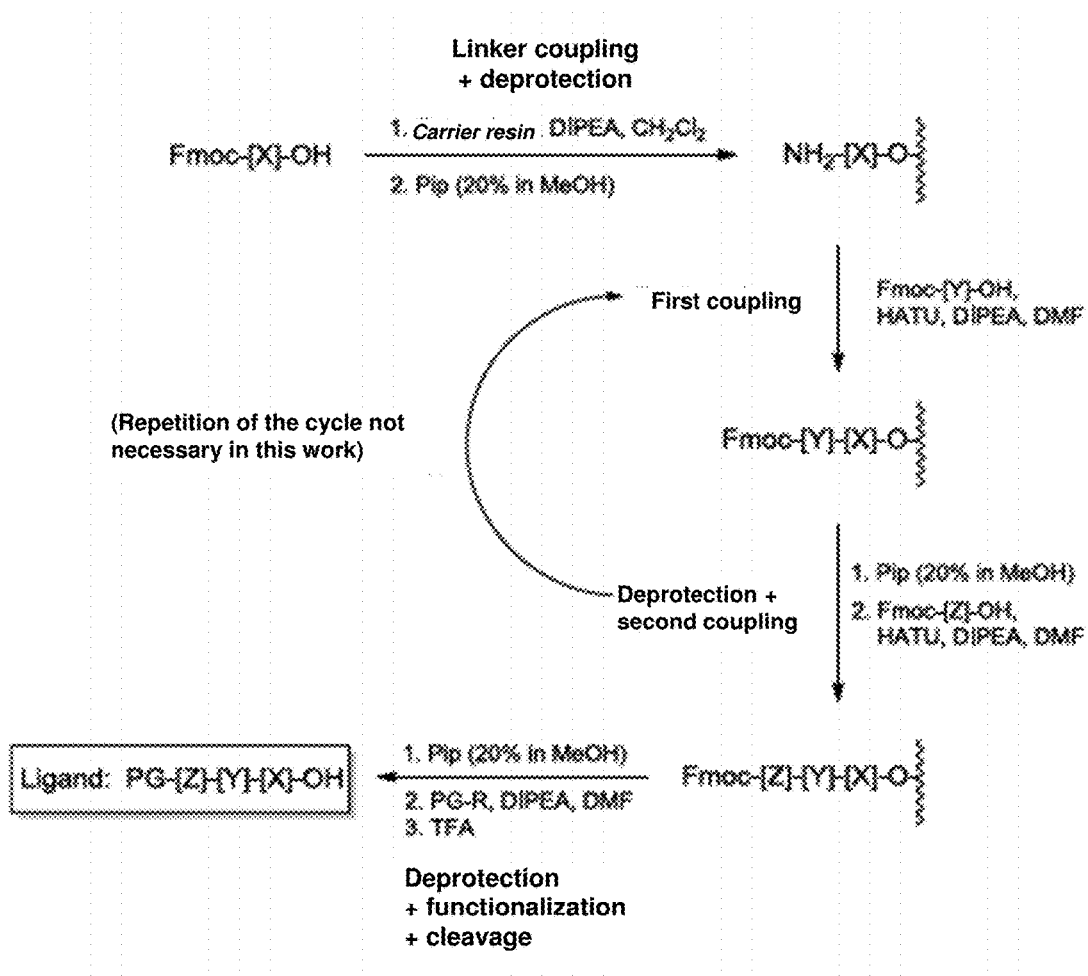

FIG. 4: Cycle of the solid phase synthesis used to form the peptide ligands.

Figure 5:
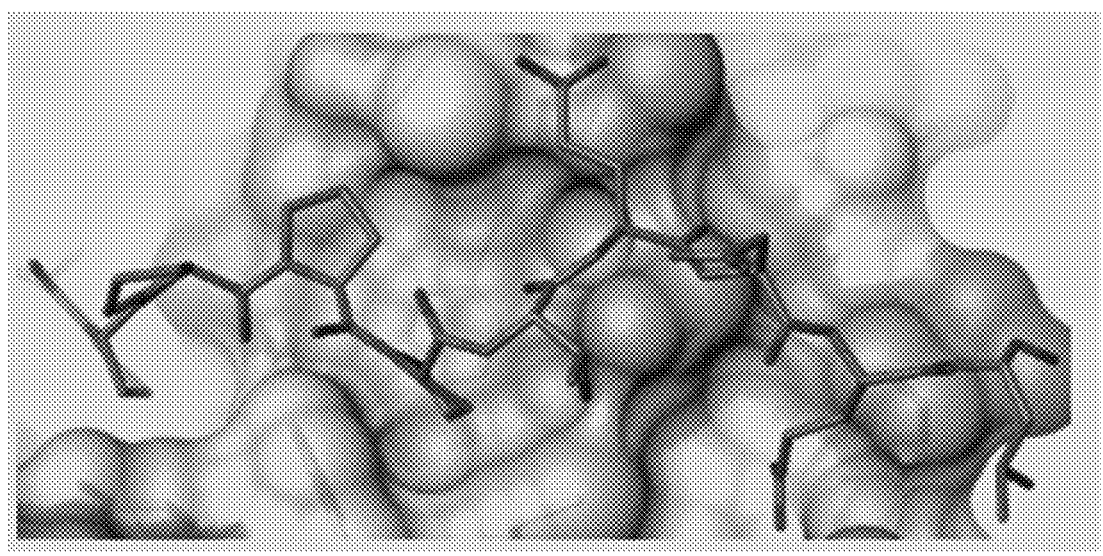

FIG. 5: Binding of SFEFPPPPTEDEL to VASP-EVH1.

Figure 6:
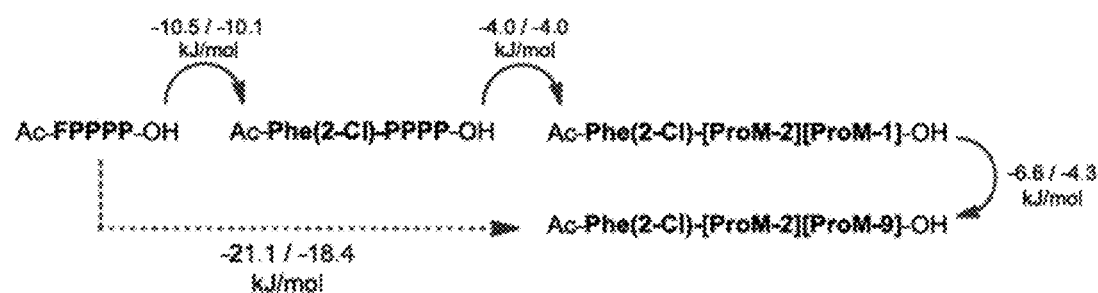

FIG. 6: Progression of the ligand optimization with respect to the gain in enthalpy $\Delta\Delta G$; left: $\Delta G$ determined by means of ITC, right: $\Delta G$: determined by means of ITC.

Figure 7:
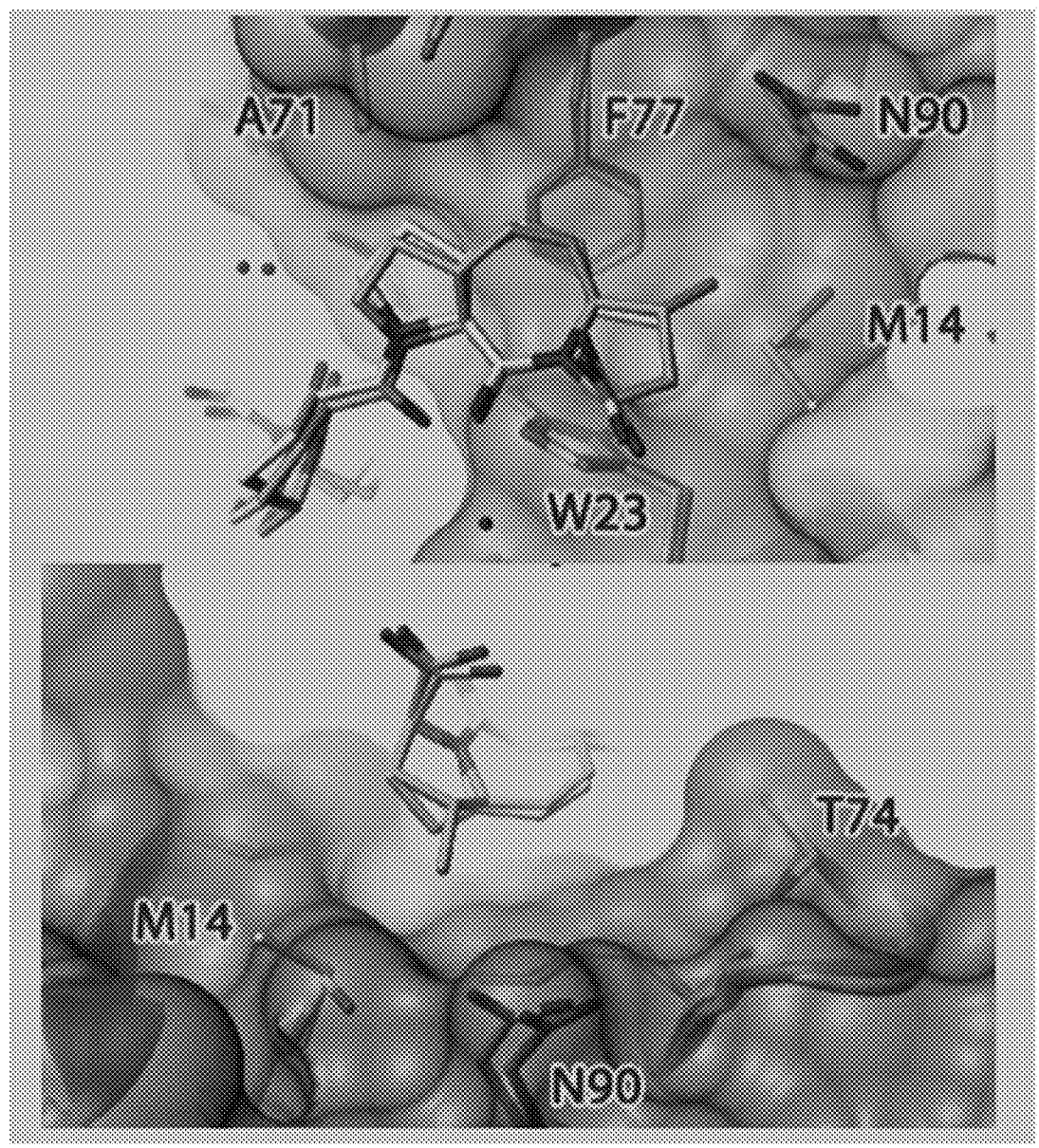

FIG. 7: Top: Binding of Ac-Phe(2-Cl)[ProM-2][ProM-1]-OH (rear) and Ac-Phe(2-Cl)-[ProM-2][ProM-9]-OH (front) to the surface of the protein, bottom: Alignment of the additional methyl group in the binding pocket.

EXAMPLES

Without being limited thereto, the invention will be explained in more detail in the following using the synthesis of the inventive compounds.

Example 1

Synthesis of the Compounds

Synthesis of Fmoc-ProM-1:

The tricyclic dipeptide mimetic Fmoc ProM 1 was synthesized as the first PPII scaffold and successfully incorporated in peptide ligands as a proline-proline equivalent.

Schema 1: Synthesis of the dipeptides 25 and dia-25 via peptide coupling and separation of the diastereomers.

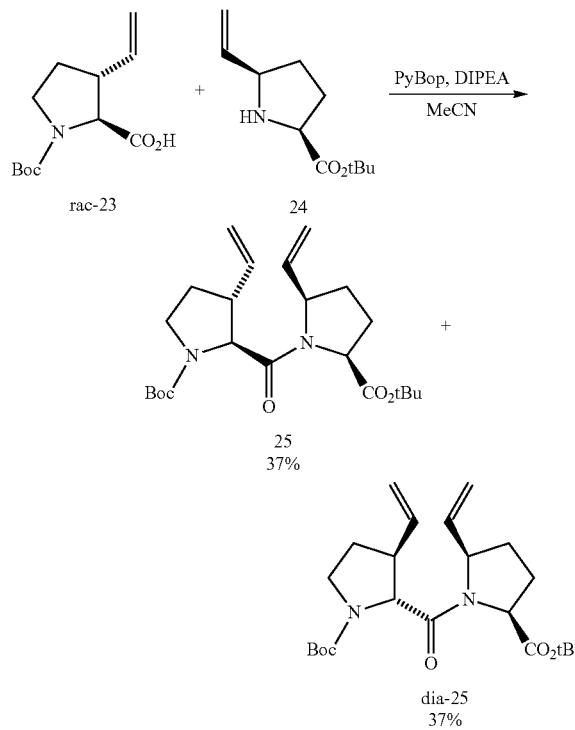

In the first step, the racemic acid building block rac-23 was coupled to the amine 24 with the use of PyBop. The resulting diastereomers 25 and dia-25 were obtained after column chromatographic separation with silica gel with a respective yield of 37% (Scheme 4.86).

Schema 2: Synthesis of Fmoc-ProM-1 via ring-closing metathesis and protecting group manipulation.

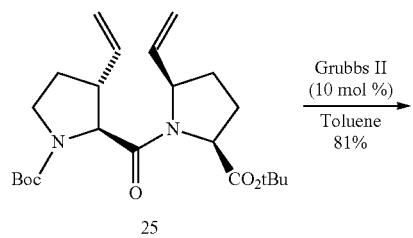

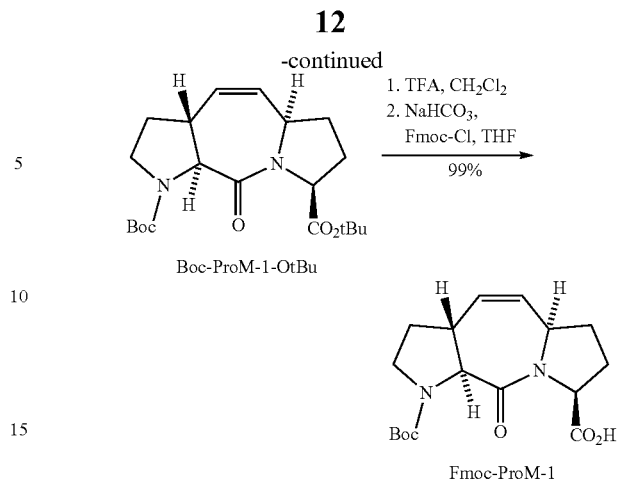

The dipeptide 25 was subsequently converted into the tricyclic Boc-ProM-1-OtBu with the use of the Grubbs II catalyst (10 mol %). The ring-closing metathesis was carried out under reflux in toluene (120° C.) and after column chromatographic purification provided the desired product in a yield of 81%. After a final conversion of Boc-ProM-1-OtBu to Fmoc-ProM-1 (TFA/NaHCO$_3$, Fmoc-Cl) the target compound was isolated in a yield of 99% (Schema 2). The purification of Fmoc-ProM-1 was performed with the aid of automated column chromatography on a Reveleris® flash system (MeOH/CH2Cl2; Gradient: 0-20%) without the addition of HOAc.

Synthesis of Fmoc-ProM-4

To do this, the racemic building block rac-67 was coupled after activation (PyBop) with the east building block 24. The corresponding dipeptide 185 was obtained as a diastereomeric mixture (dr=1:1, cis/trans) in a yield of 82%. A column chromatographic separation of the two isomers was not successful here (Schema 3).

Schema 3: Peptide coupling of the building blocks rac-67 and 24 to dipeptide 185.

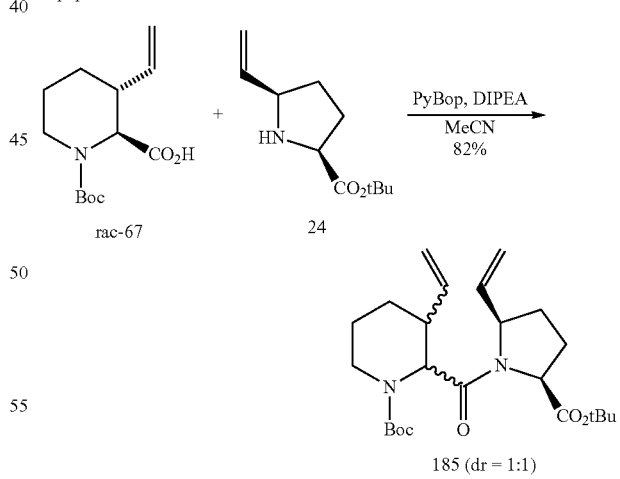

After the conversion of 185 with the Grubbs II catalyst (20 mol %) in refluxing CH2Cl2, the cyclized crude product was obtained in the form of a diastereomeric mixture of the two isomers Boc-ProM-4-OtBu and dia-Boc-ProM-4-OtBu. At this stage, the two diastereomers could be separated from one another by column chromatography with silica gel, so that it was possible to obtain the desired compound Boc-ProM-4-OtBu in 42% yield alongside dia-Boc-ProM-4-OtBu (likewise in 42%) (Schema 4).

Schema 4: Ring-closing metathesis to Boc-ProM-4-OtBu and dia-Boc-ProM-4-OtBu.

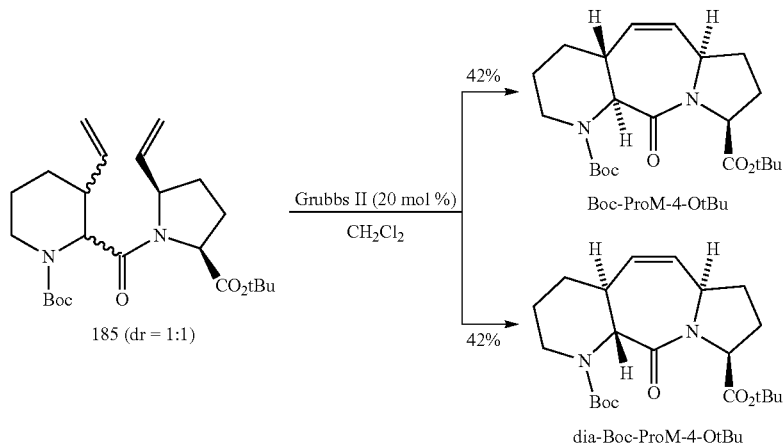

By carefully removing the solvent after the chromatographic purification, it was possible to obtain both isomers in crystalline form. The quality of the crystals was good enough to be able to determine the relative configuration via x-ray structural analysis. After successful ring closing and separation of the diastereomers, in a final step, the compound Boc-ProM-4-OtBu was to be converted by global deprotection with TFA and subsequent N-terminal Fmoc protection (NaHCO3, Fmoc-Cl) into the target mimetic Fmoc-ProM-4 (Schema 4.90). After column chromatographic purification of the crude product by means of a Reveleris® flash column chromatography system (MeOH/CH2Cl2; Gradient: 0-20%), it was possible to isolate the desired mimetic Fmoc-ProM-4 in a yield of 80%.

Schema 5: Final protecting group manipulation on Boc-ProM-4-OtBu.

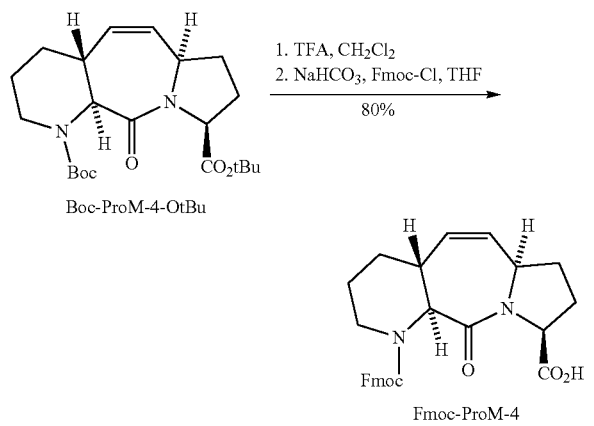

Synthesis of Fmoc-ProM-9:

In order to avoid a potentially difficult separation of the resulting diastereomers after coupling with the amine building block 70, the enantiopure compound 23 was used here for the coupling to the dipeptide instead of the racemic acid building block rac-23. From the Moc-protected proline 34, which was provided by Bayer Pharma AG (HealthCare Pharmaceuticals) in enantiopure form by means of chiral, preparative HPLC, it was possible to obtain the required N-Boc carboxylic acid 23 in a yield of 64% via protecting group manipulation over three stages (Schema 6).

Schema 6: Manufacturing of 23 from enantiopure 34.

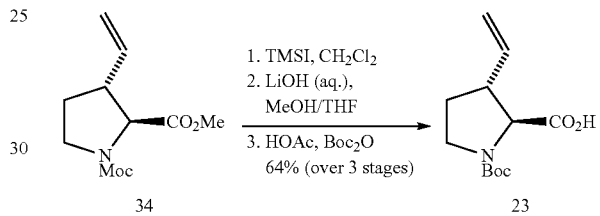

After the synthesis of the enantiopure west building block 23, said building block was coupled with the methylproline derivative 70 under standard conditions. After activation with PyBop, by reaction at room temperature and subsequent column chromatographic purification of the crude product on silica gel it was possible to isolate the desired dipeptide 192 in a yield of 87% (Schema 7).

Schema 7: Synthesis of Compound 192 by means of peptide coupling.

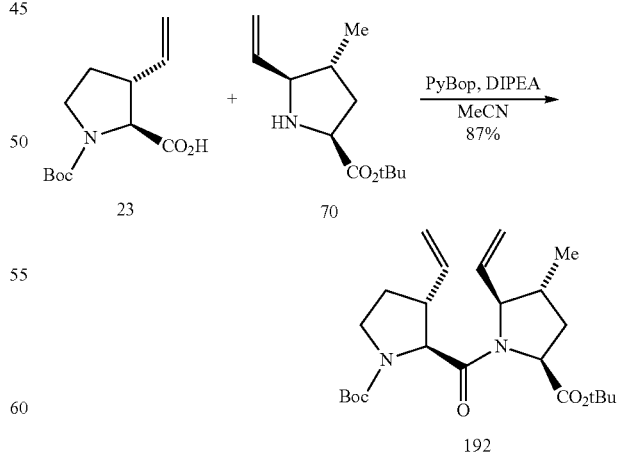

The following ring-closing metathesis of 192 was performed under formation of the tricyclic product Boc-ProM-9-OtBu with the use of 10 mol % Grubbs II catalyst in refluxing CH$_2$Cl$_2$.

A complete conversion could already be detected after eight hours. After column chromatographic purification, the cyclized product Boc ProM 9-OtBu was obtained in a yield of 82% (Schema 8). As was the case for the metathesis of Boc-ProM-4-OtBu, by carefully removing the solvent residues after the column chromatography, it was possible to obtain the substance in crystalline form, and examine its structure by means of X-ray analysis.

Schema 8: Ring-closing metathesis of 192 to the tricyclic Boc-ProM-9-OtBu.

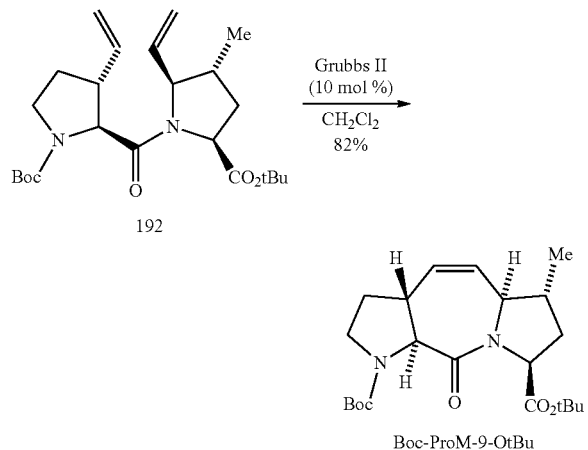

In the final step of the synthesis of the scaffold Fmoc-ProM-9, it was necessary to perform a protecting group manipulation on the tricyclic system Boc-ProM-9-OtBu. In accordance with a known procedure, the compound was globally deprotected with TFA and subsequently $_N$-terminal protected with Fmoc-Cl in a slightly alkaline (NaHCO3, pH=7-8) environment. After automated cleaning (Reveleris® system, MeOH/CH$_2$Cl$_2$; Gradient: 0-20%), it was possible to isolate the desired mimetic Fmoc-ProM-9 in a yield of 92% (Schema 9).

Schema 9: Completion of the synthesis of the mimetic Fmoc-ProM-9.

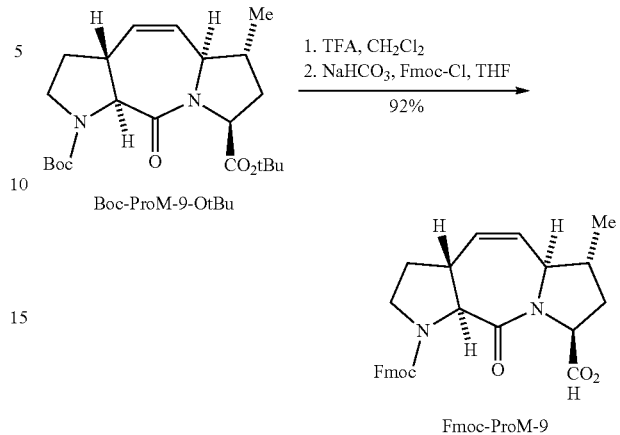

Synthesis of Fmoc-ProM-2:

To form the dipeptide compound 46, the two building blocks 45 and epi-24 were coupled with HATU and DIPEA in NMP at 85° C. in a yield of 60%. In this context it was necessary to ensure a high (dry) quality of the coupling reagent. The described conditions (30 mol % Grubbs II catalyst in CH$_2$Cl$_2$, refluxing) were modified for the ring-closing metathesis of the dipeptide 46 in order to increase the yield (of only 55%). Thus, after reaction in refluxing toluene (110-120° C.), it was possible to obtain the desired tricyclic Boc-ProM-2-OtBu in a yield of 68%. In the final step of the synthesis of Fmoc-ProM-2, the metathesis product was first globally deprotected (TFA) and N-terminal Fmoc protected under alkaline conditions (NaHCO3, pH=7-8). After the column chromatographic purification of the crude product by means of a Reveleris® flash column chromatography system (MeOH/CH2Cl2; Gradient: 0-20%), it was possible to isolate the targeted mimetic Fmoc-ProM-2 in a yield of 90%. The synthesis sequence for the formation of Fmoc-ProM-2 starting from the proline building blocks 45 and epi-24 is shown once again in Schema 4.98.

Schema 10: Synthesis of the mimetic Fmoc-ProM-2 starting from 45 and epi-24.

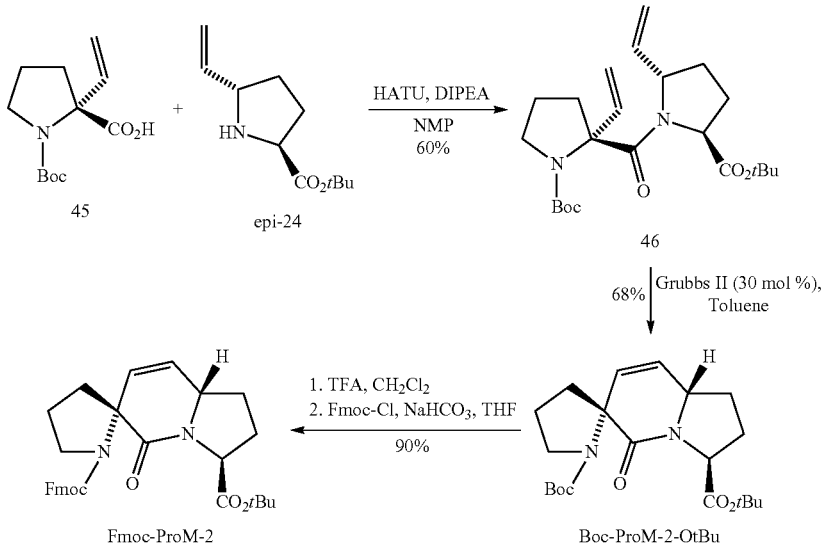

Synthesis of Fmoc-ProM-13:

The synthesis of the scaffold Fmoc-ProM-13 was performed on the basis of the following schema (Schema 11):

Schema 11: Synthesis conditions for Fmoc-ProM-13:

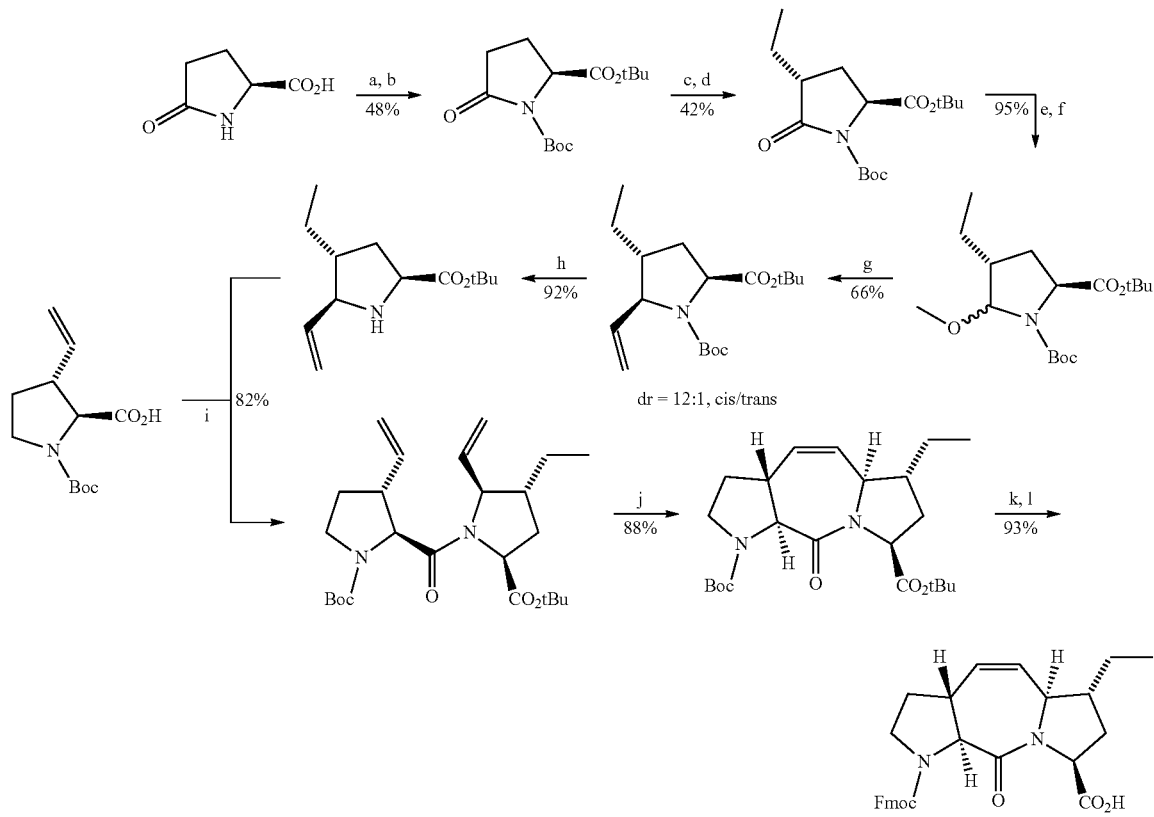

(a) HClO4, tBuOAc, RT, 65 h; (b) Boc2O, DMAP, MeCN, RT, 18 h; (c) LiHMDS, EtOTf, TPPA, THF, -78° C., 6 h; (d) TBAF, THF, 80° C., 1.5 h; (e) DIBAL-H, THF, -78° C., 2.5 h; (f) PPTS, MeOH, RT, 16 h; (g) VinylMgBr, AlCl3, BF3•OEt2, -40° C., 6 h; (h) TMSOTf, CH2Cl2, 0° C., 20 min; (i) PyBOP, DIPEA, MeCN, RT, 23 h; (j) Grubbs II, CH2Cl2, RT, 8 h; (k) TFA, CH2Cl2, 0° C., 1 h; (l) NaHCO3, FmocCl, THF, RT, 16 h.

Fmoc-ProM-13 exhibits the following structure:

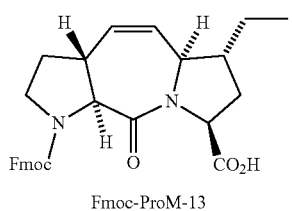

Fmoc-ProM-13

Solid Phase Peptide Synthesis and Ligand Functionalization:

Solid phase peptide synthesis was used as the method for manufacturing the compounds (SPPS). The controlled formation of a polypeptide on a solid functionalized polystyrene resin, developed by Merrifield in 1963, allows a fast, effective and, if appropriate, automated synthesis of peptides under mild conditions. For the step-by-step clarification of the coupling cycle, the corresponding sequence is shown as an example in FIG. 4. The first amino acid is thus coupled to the polystyrene resin via the C-terminal, initially against the "natural" direction of synthesis. After N-terminal deprotection (usually Boc or Fmoc protecting group strategies), another amino acid can subsequently be attached to the solid phase-bound peptide sequence by activation with a coupling reagent. This cycle can be repeated any number of times, while excess reagents are removed by washing the carrier resin. Cleavage from the resin is performed at the end to isolate the free peptide.

The synthesis of Ac-Pro-Pro-Pro-OH as a test compound (as well as the other compounds) is performed in a reactor under careful stirring using a Fmoc protective group strategy. The reactor consisted of a PET syringe sleeve, connected to a pump for suctioning off solvent residues or excess reagents, and could be freely opened and closed via a clamp for this purpose. Chloro(2'-chloro)trityl polystyrene resin beads were used as linkers. HATU in DMF served as the coupling reagent. A 20% piperidine solution (DMF) was used for Fmoc deprotection. More detailed information regarding the used reaction conditions and the washing procedures can be found in the experimental section. At the end all ligands were cleaved from the resin by adding TFA and prepared for later biological tests by subsequent lyophilization and HPLC purification. The synthesized ligands and functionalizations (NBD labeling, esterification) will be discussed in the following. Following the described procedure, starting from Fmoc protected L-proline (193) after double peptide coupling with 189 and subsequent acetylation with Ac₂O, it was thus possible to synthesize the desired triproline derivative Ac-Pro-Pro-Pro-OH on the solid phase (FIG. 4). It was nevertheless possible to confirm the successful synthesis of the substance by means of LCMS analysis.

Schema 12: Solid phase synthesis of Ac-Pro-Pro-Pro-OH starting from 193.

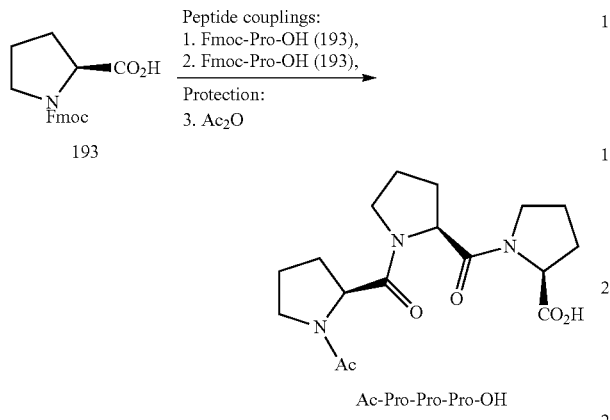

For the C-terminal esterification of the triproline Ac-Pro-Pro-Pro-OH, the substance was reacted with EtOH at room temperature under classic Steglich conditions (DCC, DMAP). After a reaction time of 23 hours, the desired ethyl ester Ac-Pro-Pro-Pro-OEt could be transferred to purification by HPLC as a crude product. It was again possible to confirm the successful synthesis of the substance by means of LCMS analysis.

Schema 13: Steglich esterification of Ac-Pro-Pro-Pro-OH to Ac-Pro-Pro-Pro-OEt.

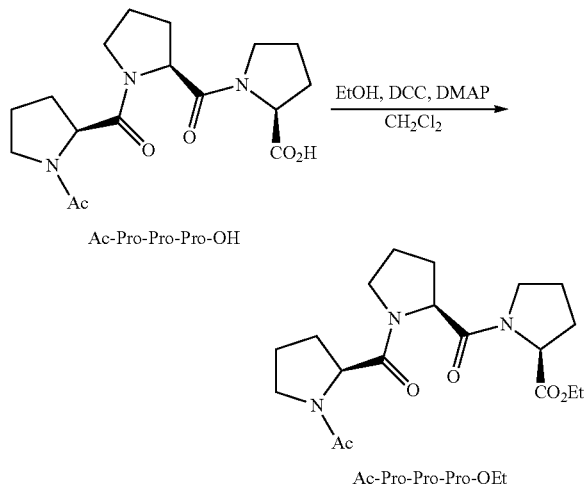

After the development of a successful methodology for esterification of proline-rich ligands of the type Ac-Pro-Pro-Pro-OEt, this procedure is used for the synthesis of the ethyl ester ligand Ac-Phe(2-Cl)-[ProM-2]-[ProM-1]-OEt. For this purpose, it was necessary to first build the system Ac-Phe(2-Cl)-[ProM-2]-[ProM-1]-OH by means of solid phase peptide synthesis, whereby the Fmoc mimetics Fmoc-ProM-1 and Fmoc-ProM-2 already discussed in previous chapters were used. The two dipeptide analogs were attached to the solid phase in this order, coupled with L-2-chloro-phenylalanine and ₙ-terminal acetylated with Ac2O (Schema 14).

Schema 14: Formation of Ac-Phe(2-Cl)-[ProM-2]-[ProM-1]-OEt.

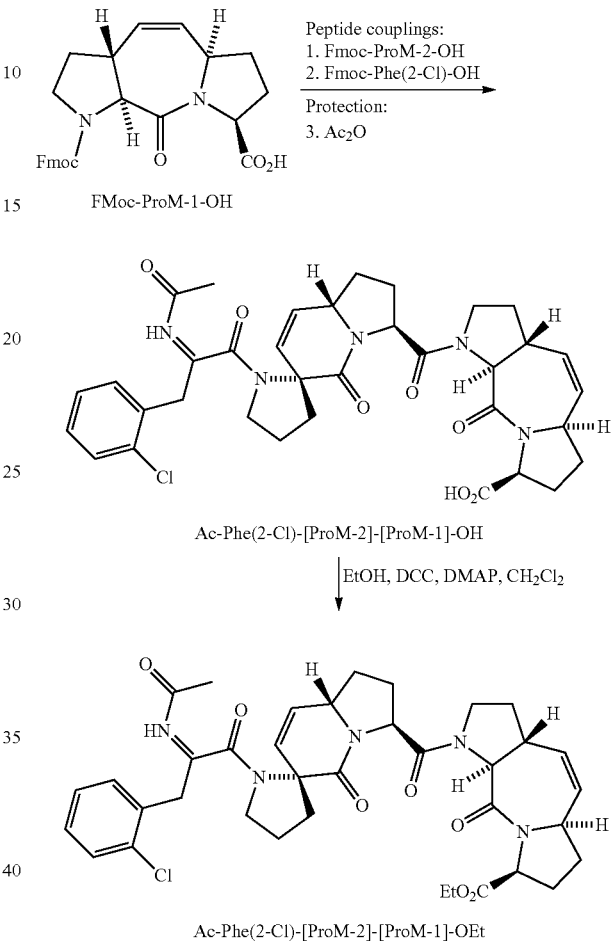

In the subsequent step, it was possible to successfully convert the ligand Ac-Phe(2-Cl)-[ProM-2]-[ProM-1]-OH into its ethyl ester derivative Ac-Phe(2-Cl)-[ProM-2]-[ProM-1]-OEt by using the Steglich esterification (verification by means of LCMS analysis). The NBD-labeled ligand Ac-Phe(2-Cl)-[ProM-2]-[ProM-1]-OEt was also manufactured according to the identical synthesis pattern (Scheme 15), so that both forms (acetylated and NBD-labeled) were now available for biological tests as ethyl esters.

Schema 15: Formation of the NBD-labeled ligand NBD-Phe(2-Cl)-[ProM-2]-[ProM-1]-OEt.

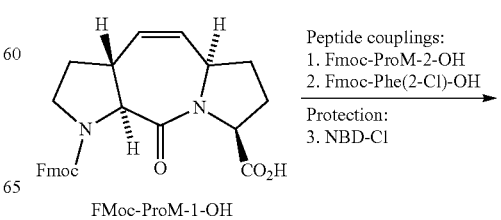

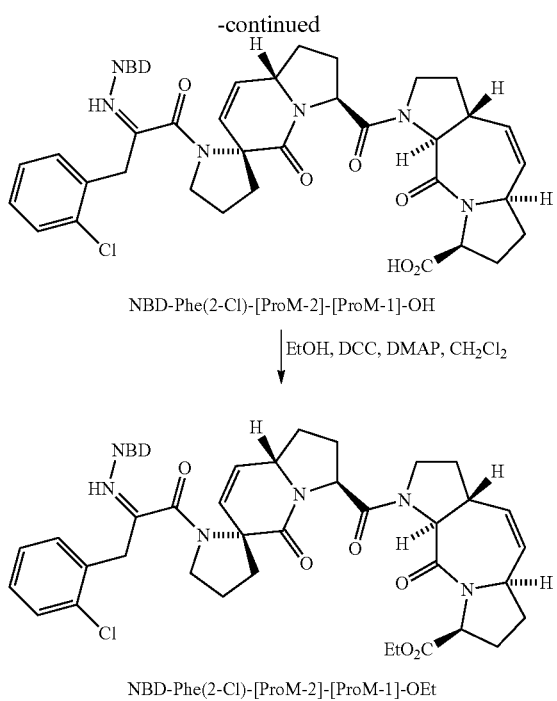

NBD-Phe(2-Cl)-[ProM-2]-[ProM-1]-OH

| EtOH, DCC, DMAP, CH$_2$Cl$_2$

NBD-Phe(2-Cl)-[ProM-2]-[ProM-1]-OEt

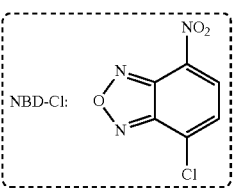

Tests Pertaining to the Solid Phase Synthesis of the Peptide Ligands:

General Test Specification (A) for the solid phase synthesis of the ligands:

Peptide coupling(s): After removing the DMF, the residue was stirred twice in succession in a piperidine solution (10 ml, 20% in MeOH) for 15 min at RT. After removing the solution, rinsing with CH2Cl2 (4×10 ml) took place. After removing the CH2Cl2, a solution of Fmoc-[Y/Z]—OH (1.2-4.0 eq.), HATU (2.0-4.0 eq.) and DIPEA (4.0-8.0 eq.) was preactivated in DMF (3 min ultrasonic bath) and stirred with the carrier resin for 25 min at RT. The LM was subsequently removed and the residue was washed with DMF and CH2Cl2 (2×10 ml each). After removing the washing solution and a possible Kaiser test, the resin was stirred with a mixture of Ac2O, DIPEA and DMF (10 ml, 1:2:7) for 10 min at RT and rinsed with DMF (3×10 ml).

The procedure for peptide coupling could be performed as often as necessary. For the ligands being discussed, the procedure was performed twice.

Protection and resin cleavage: After removing the washing solution, the residue was stirred twice in succession in a piperidine solution (10 ml, 20% in MeOH) for 15 min at RT. After removing the solution, it was rinsed with CH2Cl2 (4×10 ml) and the washing solution was removed. Subsequently, the residue was stirred with a mixture of Ac2O, DIPEA and DMF (10 ml, 1:2:7) for 10 min at RT for Ac protection, or the experimental portion 270 was shaken with a solution of NBD-CI (3.0 eq.) and DIPEA (3.0 eq.) in 2 ml DMF for 18 hours at RT for NBD protection. The LM was removed, the residue washed with DMF (3×10 ml) and the washing phase removed. For the final resin cleavage, the dry resin was stirred with (2-10 ml) TFA for two hours at RT. After removing the TFA, the carrier resin was washed with TFA and CH2Cl2 (3×10 ml each). The washing solutions were combined and evaporated to dryness. After addition of Et2O (50 ml), the product was precipitated under cooling (refrigerator), suctioned off and washed with Et2O (20 ml). Drying by lyophilization (MeCN/H2O; 10-20 ml) yielded the corresponding peptide ligand.

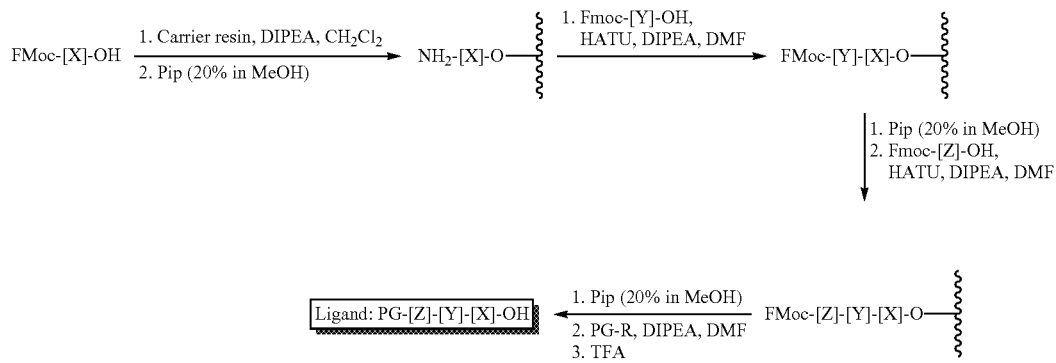

Resin coupling: In an open syringe sleeve connected to a suction mechanism, chloro-(2'-chloro)trityl polystyrene resin (1 g/1 mmol acid, capacity=1.19 mmol/g) was suspended in dry CH2Cl2 and, after addition of FMoc-[X]-OH (1.0 eq.) and DIPEA (2.0 eq.), carefully stirred for two hours at RT. The mixture was then neutralized with MeOH/DIPEA (9:1), stirred for 15 min and, after removal of the solution, washed with DMF (3×10 ml).

General Test Specification (B) for the Steglich Esterification of the Ligands:

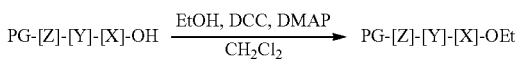

Under an argon inert gas atmosphere, the corresponding ligand (1.0 eq.) was dissolved in dry CH$_2$C$_{12}$ (2 ml) and, after addition of dry EtOH (5.0-10.0 eq.), DCC (1.0 eq.) and DMAP (0.1-0.2 eq.), stirred for 20 hours at RT. The LM was then removed under reduced pressure, the residue was absorbed in CH2Cl2 (5 ml), filtered through a glass frit (pore size=4 Å) and rinsed with $CH_2Cl_2$ (3×5 ml). Evaporation of the filtrate under reduced pressure yielded the desired ester as a crude product.

Synthesis of Ac-Phe(2-Cl)-[ProM-2]-[ProM-1]-OH According to Test Specification (A):

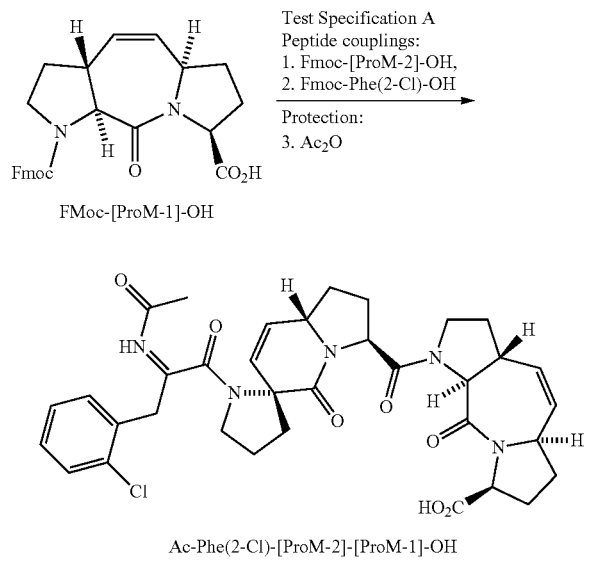

Using General Test Specification A (8.2.7.1), Fmoc-[ProM-1]-OH (0.136 g, 0.297 mmol) was coupled with chloro(2'-chloro)trityl polystyrene resin (0.250 g) by the addition of DIPEA (101 µl, 0.594 mmol) in $CH_2Cl_2$ (1.7 ml). For peptide coupling, first a solution of Fmoc-[ProM-2]-OH (0.164 g, 0.357 mmol), HATU (0.136 g, 0.357 mmol) and DIPEA (124 µl, 0.714 mmol) in DMF (1.5 ml) and then a solution of Fmoc-Phe(2-Cl)—OH (0.251 g, 0.595 mmol), HATU (0.226 g, 0.595 mmol) and DIPEA (340 µl, 1.200 mmol) in DMF (1.5 ml) were used. The free amine was then acetylated with a mixture of $Ac_2O$, DIPEA and DMF (10 ml, 1:2:7) and cleaved from the resin with 5 ml TFA. 0.075 g of the crude peptide could be obtained as a white solid. The crude product was not purified any further within the scope of the work. (Subsequent purification by means of preparative HPLC). LCMS-TOF-MS (ESI): calculated for: [M+H]+ 678.270. found: 678.268.

Synthesis of NBD-Phe(2-Cl)-[ProM-2]-[ProM-1]-OH According to Test Specification (A):

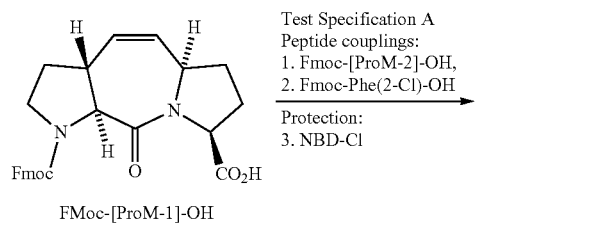

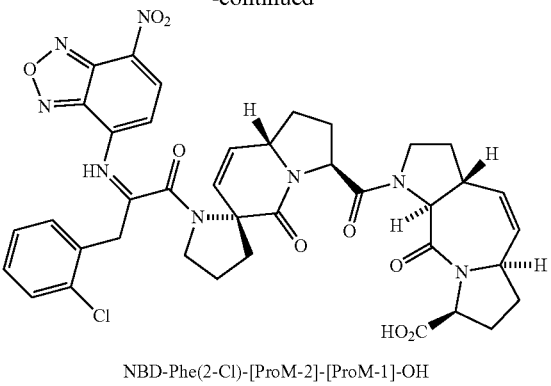

NBD-Phe(2-Cl)-[ProM-2]-[ProM-1]-OH

Using General Test Specification A (8.2.7.1), Fmoc-[ProM-1]-OH (0.075 g, 0.164 mmol) was coupled with chloro(2'-chloro)trityl polystyrene resin (0.140 g) by the addition of DIPEA (60 µl, 0.328 mmol) in $CH_2Cl_2$ (1.5 ml). For peptide coupling, first a solution of Fmoc-[ProM-2]-OH (0.090 g, 0.196 mmol), HATU (0.075 g, 0.196 mmol) and DIPEA (150 µl, 0.820 mmol) in DMF (1.5 ml) and then a solution of Fmoc-Phe(2-Cl)—OH (0.138 g, 0.328 mmol), HATU (0.125 g, 0.328 mmol) and DIPEA (120 µl, 0.656 mmol) in DMF (1.5 ml) were used. Protected with NBD-Cl (0.098 g, 0.492 mmol) and DIPEA (90 µl, 0.492 mmol) in DMF (10 ml), the free amine was then cleaved from the resin with 3 ml TFA. 0.061 g of the crude peptide could be obtained as a white solid. The crude product was not purified any further within the scope of the work. (Subsequent purification by means of preparative HPLC). LCMS-TOF-MS (ESI): calculated for: [M+H]+ 799.261. found: 799.251.

Synthesis of Ac-Phe(2-Cl)-[ProM-2]-[ProM-1]-OEt According to Test Specification (B):

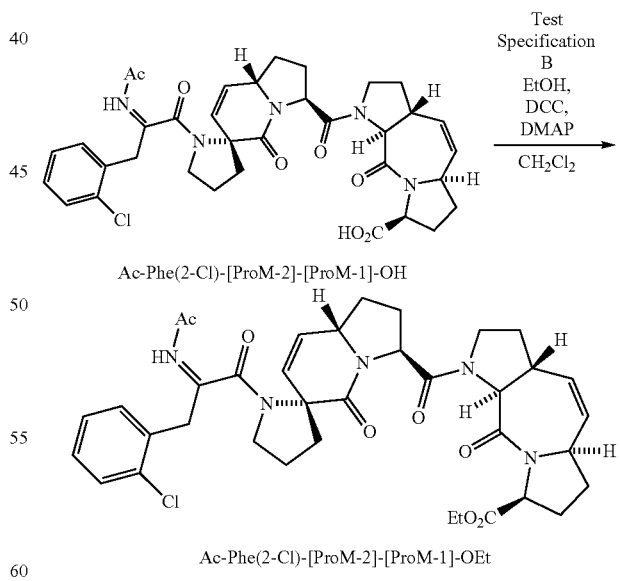

Using General Test Specification B (8.2.7.2), Ac-Phe(2-Cl)-[ProM-2]-[ProM-1]-OH (0.035 g, 0.052 mmol) was esterified with EtOH (100 µl), DCC (0.011 g, 0.052 mmol) and DMAP (0.001 g, 0.010 mmol) in $CH_2Cl_2$ (2 ml). After processing, 0.064 g of the crude product could be obtained as a white solid. The crude product was not purified any further within the scope of the work. (Subsequent purification by means of preparative HPLC). LCMS-TOF-MS (ESI): calculated for: [M+H]+ 706.301. found: 706.292. HRMS (ESI): calculated for: [M+H]+ 706.301. found: 706.302; calculated for: [M+Na]+728.283. found: 728.284.

8.2.7.8 Synthesis of NBD-Phe(2-Cl)-[ProM-2]-[ProM-1]-OEt according to Test Specification (B):

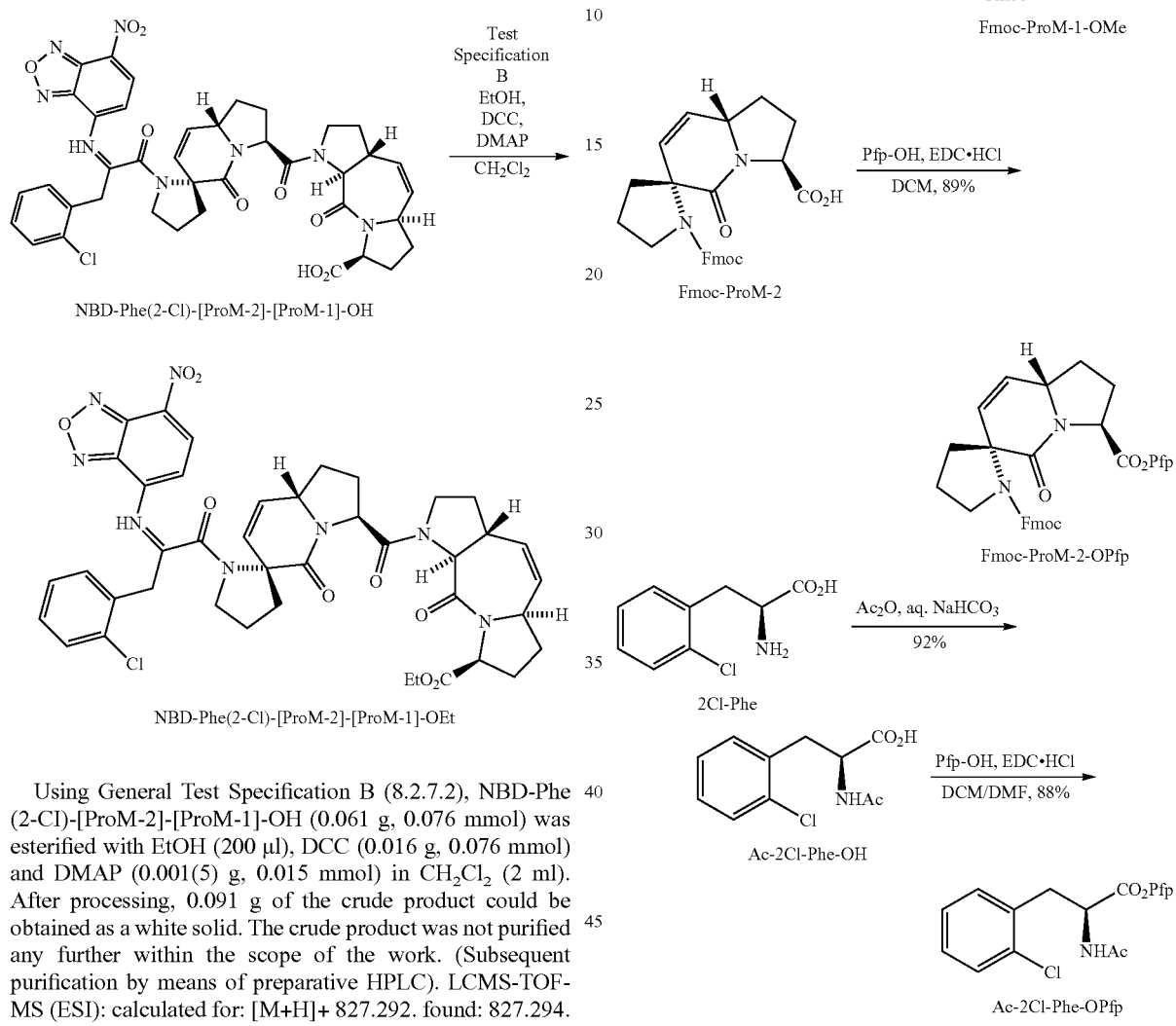

Using General Test Specification B (8.2.7.2), NBD-Phe (2-Cl)-[ProM-2]-[ProM-1]-OH (0.061 g, 0.076 mmol) was esterified with EtOH (200 µl), DCC (0.016 g, 0.076 mmol) and DMAP (0.001(5) g, 0.015 mmol) in CH$_2$Cl$_2$ (2 ml). After processing, 0.091 g of the crude product could be obtained as a white solid. The crude product was not purified any further within the scope of the work. (Subsequent purification by means of preparative HPLC). LCMS-TOF-MS (ESI): calculated for: [M+H]+ 827.292. found: 827.294.

Synthesis in a Solution:

As an alternative to solid phase coupling, the inventive compounds can be manufactured by synthesis in a solution.

The following schema is used for the protection and the activation of the compounds:

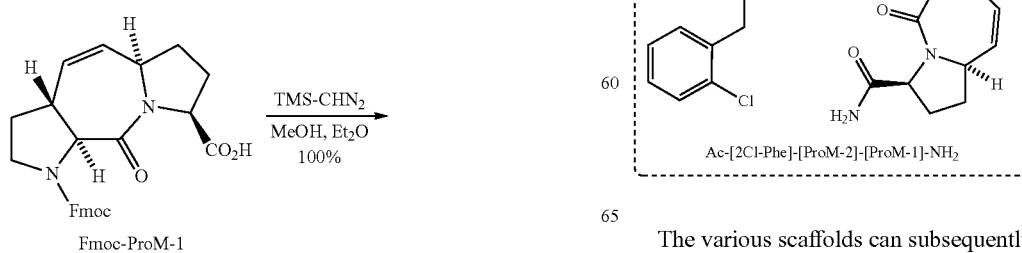

The various scaffolds can subsequently be coupled on the basis of the following schema:

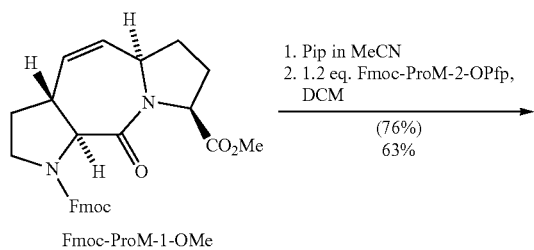

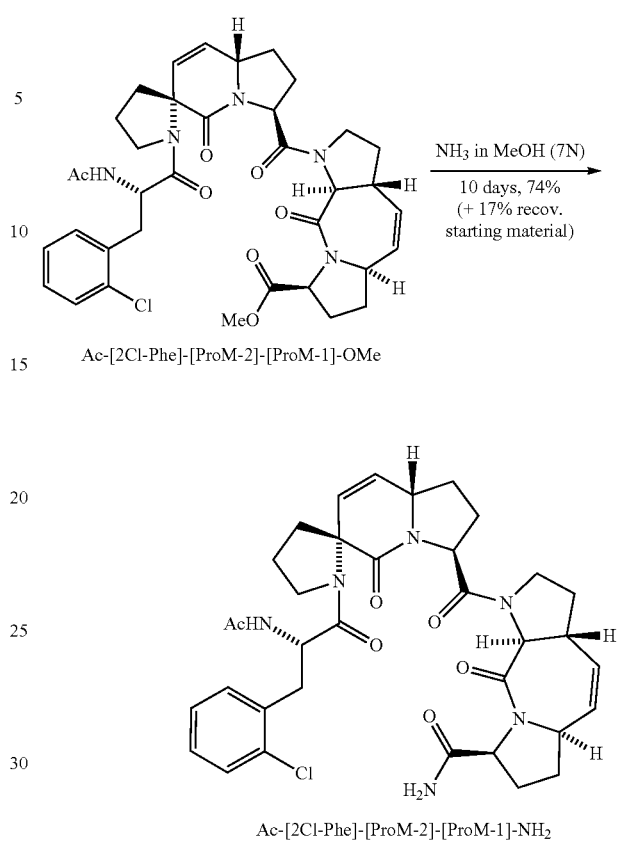

Ac-[2Cl-Phe]-[ProM-2]-[ProM-1]-OMe

Ac-[2Cl-Phe]-[ProM-2]-[ProM-1]-NH₂

Example 2

Biological Investigations

Without being limited thereto, the invention will be explained in more detail in the following using the biological properties of the inventive compounds.

As the "starting ligand" for binding studies, the "wild-type" sequence Ac-SFEFPPPPTEDEL-NH2 (an excerpt from the ActA protein of the intracellular bacterium *Listeria monocytogenes*, FIG. 5) was first reduced to the FPPPP core motif, which is recognized specifically by EVH1 domains. Consequently, for the first time, the mass of the resulting ligand Ac-FPPPP OH was in the low molecular weight range (<500 and <900 Da, depending on the definition), in the sense of a "small molecule" for affecting protein-protein interactions.

Schema 16: Pro-Pro mimetics discussed ProM scaffolds.

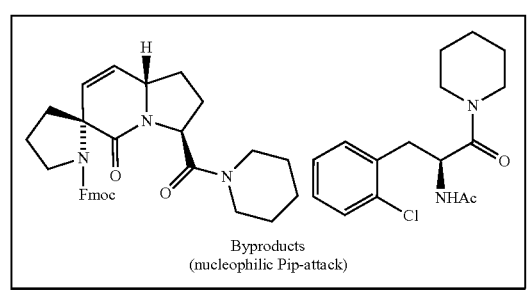

The thereby produced compounds can be modified by means of a direct amidation:

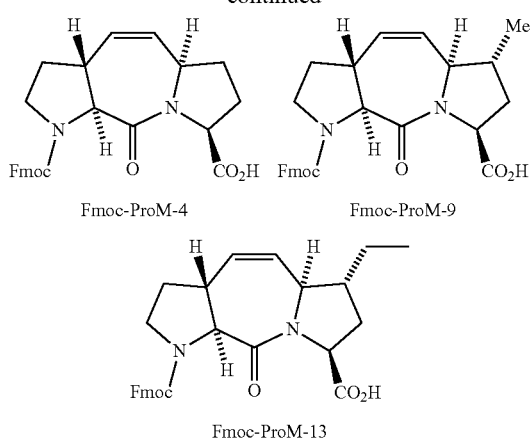

Fmoc-ProM-4    Fmoc-ProM-9

Fmoc-ProM-13

The substitution of the diproline units of the FPPPP motif with the Fmoc-ProMs was carried out. The binding affinities of the ligands to the domain were subsequently determined by means of isothermal titration calorimetry (ITC) on the basis of the dissociation constant (Kd) or the free enthalpy (ΔG) of the protein-ligand complexes. The results of the measurements were additionally checked by means of fluorescence titration (FT). A stronger binding of the respective ligand is expressed by a smaller value for Kd or a more negative value for ΔG. The correlation between the dissociation constant (Kd) and the free enthalpy (ΔG) is illustrated with the following equations:

$$K_d = \frac{[\text{Ligand}][\text{Domain}]}{[\text{Complex}]} = e^{\frac{\Delta G}{RT}}$$

The measured binding affinities of the synthetic ligands are shown in Table 5.1.

TABLE 1

Binding affinities of the various ligands with respect to the EVH-1 domain

| Ligand | ITC Kd [μM] | ITC ΔG [kJ/mol] | FT Kd [μM] | FT ΔG [kJ/mol] |
|---|---|---|---|---|
| Ac-SFEFPPPPTEDEL-NH2 | 20 | — | — | — |
| Ac-FPPPP-OH | 1300 | −16.5 | 780 | −17.7 |
| Ac-Phe(2-Cl)-PPPP-OH | 18 | −27.0 | 13 | −27.8 |
| Ac-Phe(2-Cl)-PP[ProM-1]-OH | 14.1 | −27.7 | 3.2 | −31.4 |
| Ac-Phe(2-Cl)-PP[ProM-9]-OH | 8.0 | −29.1 | 0.4 | −36.7 |
| Ac-Phe(2-Cl)-[ProM-2][ProM-1]-OH | 3.8 | −31.0 | 2.7 | −31.8 |
| Ac-Phe(2-Cl)-[ProM-2][ProM-4]-OH | 9.7 | −28.6 | 1.6 | −33.1 |
| Ac-Phe(2-Cl)-[ProM-2][ProM-9]-OH | 0.69 | −35.2 | 0.28 | −37.4 |

The shortening of the starting ligand Ac-SFEFPPPPT-EDEL-NH2 to the central FPPPP motif initially resulted in a significantly poorer binding affinity of the resulting, low molecular weight ligand Ac-FPPPP-OH (Kd[ITC]=20 μM to 1300 μM). Replacement of the terminal phenylalanine (F) by synthetic 2-chloro-phenylalanine (Phe(2-Cl)) was able to offset the poorer binding of the truncated ligands.

In further studies, the PPPP motif has now been replaced by the dipeptidic scaffolds ProM-1, ProM-2, ProM-4, ProM-9 and ProM-13. Renewed improvement of the binding affinity could be observed for the replacement of a single Pro-Pro dipeptide unit with ProM-1 or ProM-9, whereas a substitution of the front or middle Pro-Pro unit resulted in a loss of affinity. To obtain the first fully synthetic ProM-carrying peptide ligand, the two remaining prolines were replaced with the ProM-2 structure. The modeling studies were thus able to be confirmed by means of biological experiments.

ITC measurements showed that, in comparison to Ac-Phe(2-Cl)-PP[ProM-1]-OH, the ligand Ac-Phe(2-Cl)-[ProM-2][ProM-1]-OH has a four times lower Kd. A fluorescence titration confirmed the same trend, but only with an improvement of the binding affinity by a factor of 1.2. It was possible to further optimize this value by replacing ProM 1 with the ring-expanded scaffold ProM 4 (ligand: Ac-Phe(2-Cl)-[ProM-2][ProM-4]-OH) (halving of Kd). In contrast, the corresponding ITC measurements indicated poorer binding affinities, so that the ProM-1-substituted, equivalent ligand can be considered to be better binding. The determined values are nonetheless in the same size range. The structural similarity of ProM-1 and ProM-4 is thus also expressed in the affinities of their ligands to the domain. The binding studies for ring-methylated ligand Ac-Phe(2-Cl)-[ProM-2][ProM-9]-OH yielded notable results. The introduction of a single methyl group (+14 Da) into the previously best binding ligand Ac-Phe(2-Cl)-[ProM-2][ProM-1]-OH yielded an up to tenfold improved binding affinity.

A further analysis to test the dissociation constant (Kd) of a variety of other compounds was carried out by means of FT and ITC. ProM 13 coupled with ProM 2, in particular, showed a very high affinity for different target molecules.

TABLE 2

Binding affinities of the various ligands with respect to the VASP-EVH-1, EnaH-EVH-1 and EVL-EVH-1 domain.
Scaffold: Ac[2-Cl—F][ProM-2][X]-OEt

| | X: ProM-1 | X: ProM-9 | X: ProM-13 |
|---|---|---|---|
| VASP-EVH1 | | | |
| $K_D$, FT [μM] | 6.2 (0.6) | 0.78 (0.09) | 0.4 (0.1) |
| $K_D$, ITC [μM] | 9.4 (0.5) | 1.4 (0.2) | 0.49 (0.06) |
| EnaH-EVH1 | | | |
| $K_D$, FT [μM] | 4.1 (0.3) | 0.38 (0.05) | 0.18 (0.03) |
| $K_D$, ITC [μM] | 7.8 (0.4) | 0.8 (0.1) | 0.31 (0.04) |
| EVL-EVH1 | | | |
| $K_D$, FT [μM] | 4.1 (0.5) | 0.28 (0.05) | 0.13 (0.02) |
| $K_D$, ITC [μM] | 5.8 (0.7) | 0.67 (0.07) | 0.28 (0.03) |

With rational design, stereoselective synthesis and biological tests, it was thus possible to develop the first ligand that binds to EVH1 domains in the (higher) nanomolar range and which, due to its mass (e.g. of 692 Da; with restrictions), can be classified into the low molecular weight substance range.

The following FIG. 6 is intended to provide an overview of the optimization of the binding affinities by means of synthetic modification of the "wild-type" ligand. The overall progression of the optimization of the ligand Ac-Phe(2-Cl)-[ProM-2][ProM-9]-OH over multiple generations, was thus associated with an enthalpy gain of ΔΔG=−15.9 kJ/mol (determined by means of ITC).

With respect to the obtained affinity results, the additional methyl group in Ac-Phe(2-CI)-[ProM-2][ProM-9]-OH results in an improvement of the binding. The effect of the ligand substitution could also be demonstrated with the aid of the crystal structures of the ligand-domain complex. It was possible to obtain crystals of Ac-Phe(2-CI)-[ProM-2][ProM-1]-OH and Ac-Phe(2-CI)-[ProM-2][ProM-9]-OH in complex with the protein surface of a EVH1 domain and thus draw conclusions about the structural or conformational binding situation. FIG. 7 shows a superposition of the two ligands on the protein surface.

A comparison of the orientation of the two ligands on the protein surface shows that, as to be expected, the positioning of the tricyclic structures (ProM-9 ↔ ProM-1) is virtually identical. In the sense of the conceptual idea, the R-configured methyl group at Cγ additionally covers the hydrophobic surface of the protein below the proline ring, without colliding with methionine(M)-14 or asparagine(N)-90 while doing so.

Within the framework of cell experiments it could further be shown that, by replacing the carboxylic acid ligand with the ester derivative (NBD-Phe(2-CI)-[ProM-2][ProM-1]-OEt), the ability of the compound to be absorbed by the target cells could be improved. The absorption of the substance in the cell could thus be increased, without loss of the advantageous binding properties.

The following Compound III exhibits an example of an unexpected combination of advantageous properties:

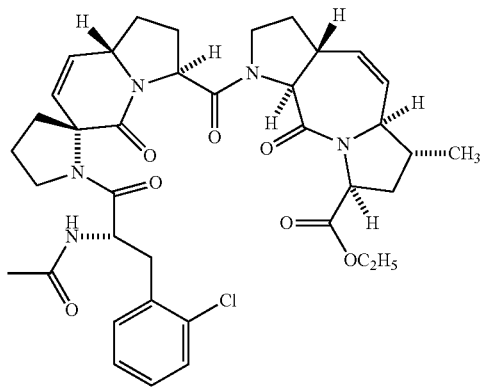 [SMILES: CCOC(=O)[C@@H]1C[C@@H](C)[C@@H]2C=C[C@H]3CCN(C(=O)[C@@H]4CC[C@H]5C=C[C@]6(CCCN6C(=O)[C@H](Cc6ccccc6Cl)NC(C)=O)C(=O)N54)[C@@H]3C(=O)N12]

This compound (in accordance with Formula III), and after further investigations also the compounds in accordance with the Formulas IV, V, VI, VII and VIII, selectively inhibit ena/VASP-EVH1-mediated protein-protein interactions. The binding data for Compound III to Ena/VASP-EVH1 are: VASP-EVH1 Kd 280 nM (better than the reference peptide by a factor of 100 (SFEFPPPPTEDEL Kd 20 μM)). This means that the ester derivative at position R3 or R6 in accordance with the general Formula I exhibits not only improved cell permeability but also improved binding properties. It could further be observed that the combination Ac-Phe(2-CI)-[ProM-2][ProM-13]-OEt exhibits a particularly strong affinity for the target.

The compounds in accordance with the Formulas III-VIII unexpectedly inhibit the chemotaxis and motility of highly invasive tumor cells. Cell culture experiments were performed with MDA MB 231 breast cancer cells. In a matrigel migration assay, it was possible to show that Example Compound III inhibits the migration of MDA MB 231 breast cancer cells by more than 90% relative to the baseline value (DMSO/no FBS gradient) (FIGS. 1 A and B).

In the process the compound was found to be non-toxic to cells (FIG. 2). The low or absent cellular toxicity likewise constitutes a surprising and advantageous property of the compounds. The inventive compounds bind to the target receptor not only with very low dissociation constants, but also with high specificity. For medical use of the compounds this is to be considered as an advantage.

The binding of the ligand to ena-EVH1 could be verified via the crystallization of the complex with Ena-EVH1 (resolution 1.02 Å) (FIG. 3). This proves that the claimed compounds exhibit exceptionally good binding properties.

The inventive compounds were further tested with respect to their stability and protein binding properties in plasma, as well as their metabolic stability. The inventive compounds surprisingly exhibit exceptionally good stability in plasma, low protein binding in plasma (only a small amount of nonspecific protein binding) and high metabolic stability, which is to be considered advantageous for clinical use.

The compounds Ac-Phe(2-CI)-[ProM-2][ProM-1]-OEt (referred to in the following as Compound 4D) and Ac-Phe(2-CI)-[ProM-2][ProM-1]-NH$_2$ (referred to in the following as Compound 4C) were examined.

An in vitro assay was performed in the plasma of mice and humans. Overall 4C was very stable in mouse and human plasma (94.7% and 80.3% remaining compound after 240 minutes of incubation). For 4D, 87.4% and 95.5% remaining compound was measured, which demonstrates its high stability in the plasma of mice and humans (half-life >240 min).

A modified ultrafiltration technique was used to assess the plasma protein binding of Compounds 4C and 4D. 4C showed very low affinity for plasma proteins, which resulted in PPB values of 5.5% and 4.5% (human and mouse). Low plasma protein binding was also observed for 4D (1.9% and 7.6% with mouse and human plasma).

The metabolic stability of 4C and 4D was tested with pooled mouse (MLM) and human liver microsomes (HLM). 4C and 4D were slowly metabolized with MLM and HLM, which resulted in $Cl_{int}$ values in the range of 34.0 and 35.6 μl/min/mg protein with MLM and 11.6 and 26.4 μl/min/mg protein with HLM.

TABLE 3

Plasma stability, nonspecific protein binding in plasma and metabolic stability of Compounds 4C and 4D.

| Assay | Species | Compound | Parameter | Result | Comment |
|---|---|---|---|---|---|
| Plasma stability | Mouse | 4C | % remaining (Tlast 240 min) | 94.7 | High stability in plasma |
| | Human | | | 80.3 | |
| | Mouse | 4D | | 87.4 | |
| | Human | | | 95.5 | |
| Plasma protein binding | Mouse | 4C | fb (bound fraction) | 5.5 | Low PPB |
| | Human | | | 4.5 | |
| | Mouse | 4D | | 1.9 | |
| | Human | | | 7.6 | |
| Liver microsomal stability | Mouse, | 4C | t½ [min] | >60 | High stability regarding Phase I metabolism |
| | Human | 4D | | >60 | |
| | Mouse | 4C | $Cl_{int}$ [μl/min/mg Protein] | 34.0 | |
| | Human | | | 11.6 | |
| | Mouse | 4D | | 35.6 | |
| | Human | | | 26.4 | |

The invention claimed is:

1. A compound in accordance with Formula I:

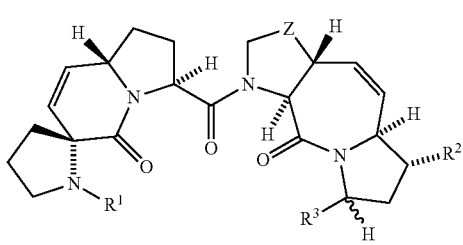

wherein:
- $R^1$: is H, acyl, peptidyl, sulfonyl, alkyl, aryl or heteroaryl, wherein the acyl, peptidyl, sulfonyl, alkyl, aryl or heteroaryl substituents are optionally substituted with halogen, acyl, carboxyl, amino, carbamoyl, OH, O-alkyl, SH, S-alkyl, alkyl, aryl or heteroaryl;
- $R^2$: is alkyl, cycloalkyl, alkenyl, alkynyl, halogen, O-alkyl, S-alkyl, aryl or heteroaryl, wherein the alkyl, cycloalkyl, alkenyl, alkynyl, O-alkyl, S-alkyl, aryl or heteroaryl substituents are optionally substituted with halogen, acyl, carboxyl, amino, carbamoyl, OH, O-alkyl, SH, S-alkyl, alkyl, aryl or heteroaryl;
- $R^3$: is alkyl; acyl or a carboxylic acid derivative in accordance with C(=O)X, wherein X is OH, O-alkyl, O-aryl, heteroaryl, NRR' or NROR', wherein R and R' are independently H or alkyl; and
- Z: is $CH_2$ or $CH_2CH_2$.

2. A compound according to claim 1 in accordance with Formula I-a:

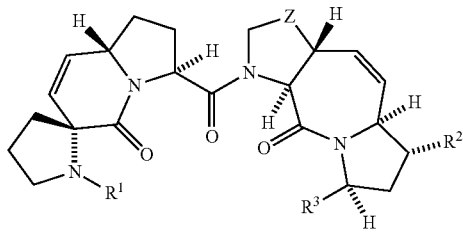

wherein:
- $R^1$: is H, acyl, peptidyl, sulfonyl, alkyl, aryl or heteroaryl, wherein the acyl, peptidyl, sulfonyl, alkyl, aryl or heteroaryl substituents are optionally substituted with halogen, acyl, carboxyl, amino, carbamoyl, OH, O-alkyl, SH, S-alkyl, alkyl, aryl or heteroaryl;
- $R^2$: is alkyl, cycloalkyl, alkenyl, alkynyl, halogen, O-alkyl, S-alkyl, aryl or heteroaryl, wherein the alkyl, cycloalkyl, alkenyl, alkynyl, O-alkyl, S-alkyl, aryl or heteroaryl substituents are optionally substituted with halogen, acyl, carboxyl, amino, carbamoyl, OH, O-alkyl, SH, S-alkyl, alkyl, aryl or heteroaryl;
- $R^3$: is alkyl; acyl or a carboxylic acid derivative in accordance with C(=O)X, wherein X is OH, O-alkyl, O-aryl, heteroaryl, NRR' or NROR', wherein R and R' are independently H or alkyl; and
- Z: is $CH_2$ or $CH_2CH_2$.

3. A compound according to claim 1 in accordance with Formula II:

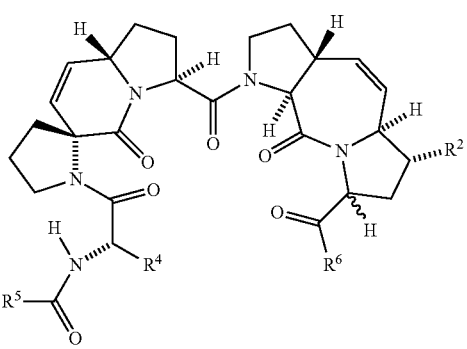

wherein:
- $R^2$: is alkyl, cycloalkyl, alkenyl, alkynyl, halogen, O-alkyl, S-alkyl, aryl or heteroaryl, wherein the alkyl, cycloalkyl, alkenyl, alkynyl, O-alkyl, S-alkyl, aryl or heteroaryl substituents are optionally substituted with halogen, acyl, carboxyl, amino, carbamoyl, OH, O-alkyl, SH, S-alkyl, alkyl, aryl or heteroaryl;
- $R^4$: H, alkyl, aryl or a heterocyclic substituent, wherein the alkyl, aryl or heterocyclic substituents are optionally substituted with halogen, acyl, carboxyl, amino, carbamoyl, OH, O-alkyl, SH, S-alkyl, alkyl, aryl or heteroaryl;
- $R^5$: H, alkyl or a substituted alkyl radical;
- $R^6$: OH, O-alkyl, O-aryl, heteroaryl, NRR' or NROR', wherein R and R' are independently H or alkyl.

4. A compound according to claim 1 in accordance with Formula II-a:

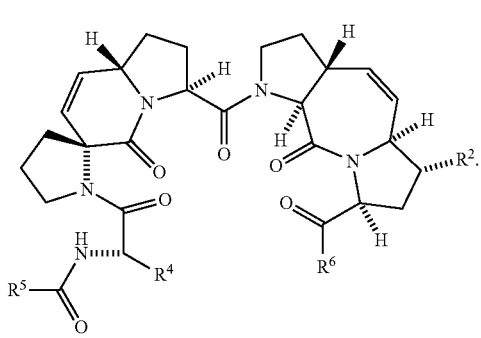

wherein
- $R^2$: is alkyl, cycloalkyl, alkenyl, alkynyl, halogen, O-alkyl, S-alkyl, aryl or heteroaryl, wherein the alkyl, cycloalkyl, alkenyl, alkynyl, O-alkyl, S-alkyl, aryl or heteroaryl substituents are optionally substituted with halogen, acyl, carboxyl, amino, carbamoyl, OH, O-alkyl, SH, S-alkyl, alkyl, aryl or heteroaryl;
- $R^4$: is H, alkyl, aryl or a heterocyclic substituent, wherein the alkyl, aryl or heterocyclic substituents are optionally substituted with halogen, acyl, carboxyl, amino, carbamoyl, OH, O-alkyl, SH, S-alkyl, alkyl, aryl or heteroaryl;
- $R^5$: is H, alkyl or a substituted alkyl radical; and
- $R^6$: is OH, O-alkyl, O-aryl, heteroaryl, NRR' or NROR', wherein R and R' are independently H or alkyl.

5. A compound according to claim 1 in accordance with Formula I, wherein $R^2$: is alkyl, cycloalkyl, alkenyl, alkynyl or halogen.

6. A compound according to claim 5 in accordance with Formula I, wherein $R^2$ is alkyl, selected from the group consisting of $CH_3$, $C_2H_5$ and $C_3H_7$.

7. A compound according to claim 3 in accordance with Formula II, wherein $R^4$: is $CH_2$-phenyl, wherein the phenyl group is substituted at the ortho position.

8. A compound according to claim 3 in accordance with Formula II, wherein $R^6$ is O-alkyl; O-aryl; NRR' or NROR', wherein R and R' are independently H or alkyl.

9. A compound according to claim 3 in accordance with Formula II, wherein $R^6$: is O—$CH_3$, O—$C_2H_5$ or $NH_2$.

10. A compound according to claim 3 in accordance with Formula III-VIII:

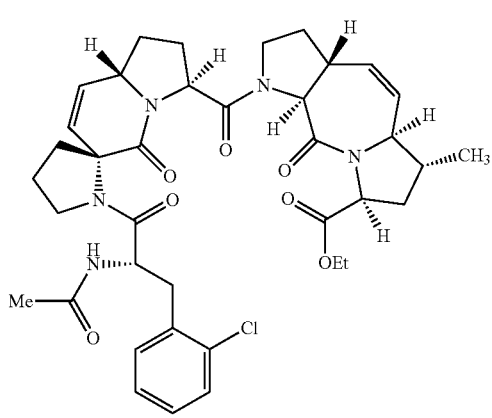

III

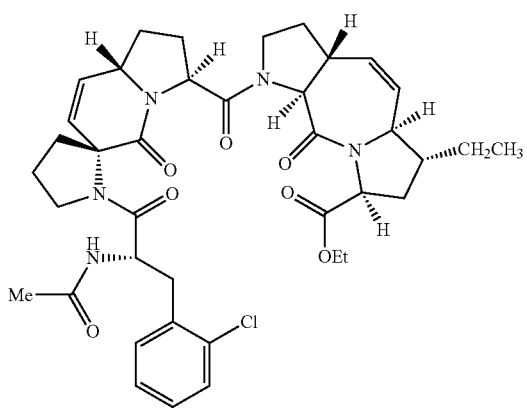

IV

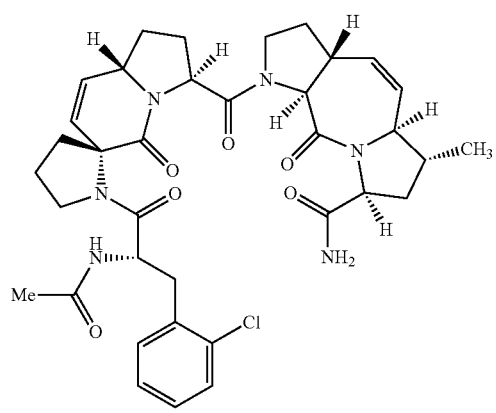

V

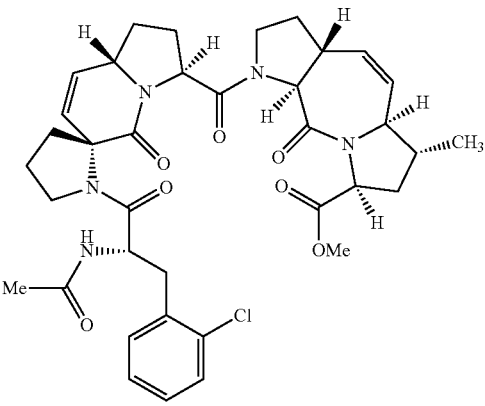

VI

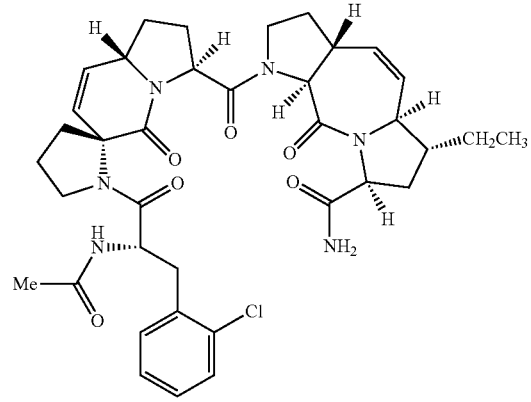

VII

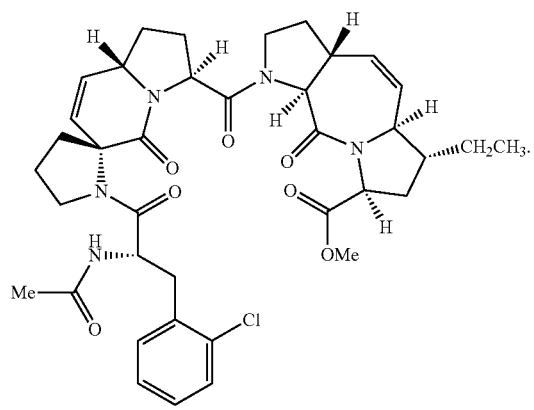

VIII

11. A pharmaceutical composition comprising a compound according to claim 1, together with a pharmaceutically acceptable carrier.

12. A method of treating metastasis of a tumor in a subject comprising administering to the subject a compound according to claim 1, wherein the tumor is a breast cancer tumor.

13. The compound according to claim 1, wherein Z is $CH_2$.

14. The compound according to claim 3, wherein $R^4$ is —$CH_2$-aryl or —$CH_2$-heteroaryl.

15. The compound according to claim 4, wherein $R^4$ is —$CH_2$-aryl or —$CH_2$-heteroaryl.

16. The compound according to claim 7, wherein the substituent positioned at the ortho position of the phenyl group is a halogen.

17. The compound according to claim 16, wherein the halogen is Cl.

18. The compound according to claim 14, wherein $R^4$ is —CH$_2$-phenyl, —CH$_2$-1-naphthyl or —CH$_2$-3-indolyl.

19. The compound according to claim 15, wherein $R^4$ is —CH$_2$-phenyl, —CH$_2$-1-naphthyl or —CH$_2$-3-indolyl.

* * * * *